(12) United States Patent
Charier et al.

(10) Patent No.: US 8,226,942 B2
(45) Date of Patent: Jul. 24, 2012

(54) PDGF FUSION PROTEINS INCORPORATED INTO FIBRIN FOAMS

(75) Inventors: Gaëlle Charier, Zürich (CH); Manuela Müller-Maissen, Zürich (CH); Anna Jen, Zug (CH)

(73) Assignee: Kuros Biosurgery AG, Zurich (CH)

( * ) Notice: Subject to any disclaimer, the term of this patent is extended or adjusted under 35 U.S.C. 154(b) by 361 days.

(21) Appl. No.: 12/342,420

(22) Filed: Dec. 23, 2008

(65) Prior Publication Data

US 2009/0169539 A1 Jul. 2, 2009

Related U.S. Application Data

(63) Continuation of application No. PCT/EP2008/068185, filed on Dec. 22, 2008.

(60) Provisional application No. 61/017,409, filed on Dec. 28, 2007.

(51) Int. Cl.
*A61K 38/48* (2006.01)
(52) U.S. Cl. .......................... 424/94.64; 424/94; 530/350
(58) Field of Classification Search .................. None
See application file for complete search history.

(56) References Cited

U.S. PATENT DOCUMENTS

| | | | |
|---|---|---|---|
| 4,086,196 A | 4/1978 | Tregear | |
| 4,613,665 A | 9/1986 | Larm | |
| 4,810,784 A | 3/1989 | Larm | |
| 5,100,668 A | 3/1992 | Edelman et al. | |
| 5,171,670 A | 12/1992 | Kronenberg et al. | |
| 5,202,247 A | 4/1993 | Kilburn et al. | |
| 5,206,023 A | 4/1993 | Hunziker | |
| 5,428,014 A | 6/1995 | Labroo et al. | |
| 5,504,001 A | 4/1996 | Foster | |
| 5,529,986 A | 6/1996 | Larsson et al. | |
| 5,561,982 A | 10/1996 | Tunkel et al. | |
| 5,582,862 A | 12/1996 | Reed | |
| 5,606,031 A | 2/1997 | Lile et al. | |
| 5,641,670 A | 6/1997 | Treco et al. | |
| 5,693,341 A | 12/1997 | Schroeder et al. | |
| 5,747,456 A | 5/1998 | Chorev et al. | |
| 5,770,194 A | 6/1998 | Edwardson et al. | |
| 5,773,577 A | 6/1998 | Cappello | |
| 5,814,603 A | 9/1998 | Oldenburg et al. | |
| 5,840,837 A | 11/1998 | Krstenansky et al. | |
| 5,874,308 A | 2/1999 | Kilburn et al. | |
| 5,874,500 A | 2/1999 | Rhee et al. | |
| 5,877,153 A | 3/1999 | Harris et al. | |
| 5,958,874 A | 9/1999 | Clark et al. | |
| 6,054,122 A | 4/2000 | MacPhee et al. | |
| 6,117,425 A | 9/2000 | MacPhee et al. | |
| 6,136,564 A | 10/2000 | Kopetzki et al. | |
| 6,150,328 A | 11/2000 | Wang et al. | |
| 6,197,325 B1 | 3/2001 | MacPhee et al. | |
| 6,303,138 B1 | 10/2001 | Peterson et al. | |
| 6,331,422 B1 * | 12/2001 | Hubbell et al. | 435/193 |
| 6,468,543 B1 | 10/2002 | Gilbertson et al. | |
| 6,468,731 B1 | 10/2002 | Hubbell | |
| 6,559,119 B1 | 5/2003 | Burgess et al. | |
| 6,607,740 B1 | 8/2003 | Hubbell et al. | |
| 6,608,293 B2 | 8/2003 | Kuderer | |
| 6,663,870 B2 | 12/2003 | Hart et al. | |
| 6,723,344 B2 | 4/2004 | Sakiyama-Elbert et al. | |
| 6,894,022 B1 * | 5/2005 | Hubbell et al. | 530/350 |
| 6,960,452 B2 | 11/2005 | Hubbell et al. | |
| 7,026,292 B1 | 4/2006 | Lee et al. | |
| RE39,192 E | 7/2006 | MacPhee et al. | |
| RE39,298 E | 9/2006 | MacPhee et al. | |
| RE39,321 E | 10/2006 | MacPhee et al. | |
| 7,189,410 B1 | 3/2007 | Drohan et al. | |
| 7,196,054 B1 | 3/2007 | Drohan et al. | |
| 7,208,179 B1 | 4/2007 | Drohan et al. | |
| 7,229,826 B2 | 6/2007 | Kale et al. | |
| 7,229,959 B1 | 6/2007 | Drohan et al. | |
| 7,241,730 B2 | 7/2007 | Hubbell et al. | |
| 7,247,609 B2 * | 7/2007 | Lutolf et al. | 514/13.6 |
| 7,601,685 B2 * | 10/2009 | Hubbell et al. | 514/1.1 |
| 2002/0168718 A1 | 11/2002 | Hubbell et al. | |
| 2003/0012818 A1 | 1/2003 | Schense et al. | |
| 2003/0103957 A1 | 6/2003 | McKerracher | |
| 2003/0119186 A1 | 6/2003 | Hubbell et al. | |
| 2003/0166833 A1 | 9/2003 | Lutolf et al. | |
| 2003/0187232 A1 | 10/2003 | Hubbell et al. | |
| 2003/0190364 A1 | 10/2003 | Panitch et al. | |
| 2004/0082513 A1 | 4/2004 | Hubbell et al. | |
| 2005/0010297 A1 | 1/2005 | Watson et al. | |
| 2005/0148763 A1 | 7/2005 | Sekimori et al. | |
| 2005/0175665 A1 | 8/2005 | Hunter et al. | |
| 2005/0180957 A1 * | 8/2005 | Scharp et al. | 424/93.7 |
| 2006/0147443 A1 | 7/2006 | Schense et al. | |
| 2006/0148704 A1 | 7/2006 | Schense et al. | |
| 2006/0168718 A1 | 8/2006 | Watson et al. | |
| 2007/0010440 A1 | 1/2007 | Schense et al. | |
| 2007/0179093 A1 | 8/2007 | Lutolf et al. | |
| 2007/0202178 A1 | 8/2007 | Schense et al. | |

FOREIGN PATENT DOCUMENTS

DE 200 10 297 10/2000

(Continued)

OTHER PUBLICATIONS

Kwon-Soo Ha et al. (The J. of Biological Chem., vol. 268, No. 14, May 1993, pp. 10534-10539).*

(Continued)

*Primary Examiner* — Hope Robinson
(74) *Attorney, Agent, or Firm* — Pabst Patent Group LLP

(57) ABSTRACT

Compositions for wound healing, use of the compositions, and kits and methods of using thereof are described herein. In a preferred aspect, the compositions are suitable for use in a method for forming a fibrin matrix or foam that can be applied or injected at the site of need. In another preferred aspect, the compositions are also suitable for use in methods for forming enhanced controlled delivery fibrin matrices that can be administered as gels or foams.

39 Claims, 11 Drawing Sheets

FOREIGN PATENT DOCUMENTS

| | | |
|---|---|---|
| EP | 0 530 804 | 3/1993 |
| EP | 0 605 963 | 7/1994 |
| EP | 725 145 | 8/1996 |
| EP | 950 665 | 10/1999 |
| JP | 7-196925 | 8/1995 |
| WO | WO 89/00051 | 1/1989 |
| WO | WO 89/09787 | 10/1989 |
| WO | WO 90/05177 | 5/1990 |
| WO | WO 90/09783 | 9/1990 |
| WO | WO 92/02620 | 2/1992 |
| WO | WO 92/09301 | 6/1992 |
| WO | WO 92/22312 | 12/1992 |
| WO | WO 94/20133 | 9/1994 |
| WO | WO 95/05396 | 2/1995 |
| WO | WO 95/23611 | 9/1995 |
| WO | WO 96/17633 | 6/1996 |
| WO | WO 97/18314 | 5/1997 |
| WO | WO 97/24445 | 7/1997 |
| WO | WO 98/31788 | 7/1998 |
| WO | WO 98/43686 | 10/1998 |
| WO | WO 99/03887 | 1/1999 |
| WO | WO 99/21588 | 5/1999 |
| WO | WO 99/31137 | 6/1999 |
| WO | WO 00/06534 | 2/2000 |
| WO | WO 00/10596 | 3/2000 |
| WO | WO 00/44808 | 8/2000 |
| WO | WO 00/49159 | 8/2000 |
| WO | WO 00/64481 | 11/2000 |
| WO | WO 01/12230 | 2/2001 |
| WO | WO 01/66164 | 9/2001 |
| WO | WO 01/76558 | 10/2001 |
| WO | WO 01/81415 | 11/2001 |
| WO | WO 01/83522 | 11/2001 |
| WO | WO 02/085422 | 10/2002 |
| WO | WO 03/040235 | 5/2003 |
| WO | WO 03/052091 | 6/2003 |
| WO | WO 2004/071543 | 8/2004 |
| WO | WO 2006/072622 | 7/2006 |
| WO | WO 2006/072623 | 7/2006 |

OTHER PUBLICATIONS

Adams, et al., "Roles of ephrinB ligands and EphB receptors in cardiovascular development: demarcation of arterial/venous domains, vascular morphogenesis, and sprouting angiogenesis", *Genes & Development* 13:295-306 (1999).

Baumgartner, et al., "Constitutive expression of phVEGF165 after intramuscular gene transfer promotes collateral vessel development in patients with critical limb ischemia", *Circulation*, 97:1114-1123 (1998).

Besson, et al., "Synthetic peptide substrates for a conductimetric assay of Pseudomonas aeruginosa elastase", *Analytical Biochemistry*, 237(2):216-223 (1996).

Blaess, et al., "Structural analysis of the sixth immunoglobulin-like domain of mouse neural cell adhesion molecule L1 and its interactions with alpha(v)beta3, alpha(IIb)beta3, and alpha5beta1 integrins", *J Neurochem*, 71:2615-2625 (1998).

Bonadio, et al., "Localized, direct plasmid gene delivery in vivo: prolonged therapy results in reproducible tissue regeneration", *Nat Med.*, 5(7):753-9 (1999).

Bone Morphogenic proteins, in R&D Systems' 1999 catalog retrieved from www.rndsystems.com/mini_review_detail_ objectnarne_MR99_BMPs.aspx#Structure, onJul. 13, 2007.

Borrajo, et al., "Derivatized cyclodextrins as peptidometics: Influence on neurite growth", *Bioorganic and Medicinal Chemistry Letters*, 7:1185-90 (1997).

Borth, et al., "Lipoprotein (a) is a substrate for factor XIIIa and tissue transglutaminase", *J. Biol. Chem.*, 266 (27): 18149-18153 (1991).

Brooks, et al., "Requirement of vascular integrin $\alpha v\beta 3$ for angiogenesis", *Science*, 264:569-571 (1994).

Bruckner, "EphrinB ligands recruit GRIP family PDZ adaptor proteins into raft membrane microdomains", *Neuron*, 22:511-524 (1999).

Calderwood, et al.. "Integrins and actin filaments: reciprocal regulation of cell adhesion and signaling", *J Biol Chem*, 275:22607-22610 (2000).

Camarata, et al., "Sustained release of nerve growth factor from biodegradable polymer microspheres", *Neurosurgery Online*, 30(3) 313-319 (1992).

Cardin, et al., "Molecular modeling of protein-Glycosaminoglycan interactions", *Arterioscler Thromb Vasc Biol*, 9:21-32 (1989).

Carr et al., "Effects of ionic and nonionic contrast media on clot structure, platelet function and thrombolysis mediated by tissue plasminogen activator in plasma clots", *Haemostasis*, 25(4):172-81 (1995).

Chen, et al., "The Golgi sialoglycoprotein MG160, expressed in Pichia pastoris, does not require complex carbohydrates and sialic acid for secretion and basic fibroblast growth factor binding", *Biochem Biophys Res Commun* 234(1): 68-72 (1997).

Conover, et al., "Disruption of Eph/ephrin signaling affects migration and proliferation in the adult subventricular zone", *Nature Neuroscience*, 3(11):1091-3324 (2000).

Coombs, et al., "Directing sequence-specific proteolysis to new targets. The influence of loop size and target sequence on selective proteolysis by tissue-type plasminogen activator and urokinase-type plasminogen activator", *J. Biol. Chem.*, 273(8):4323-4328 (1998).

Coussons, et al. "Factors that govern the specificity of transglutaminase-catalysed modification of proteins and peptides", *Biochemical L.*, 282:929-30 (1992).

Dalva, et al., "EphB receptors interact with NMDA receptors and regulate excitatory synapse formulation", *Cell*, 103:945-956 (2000).

Deblois, et al., "Heparin-fibroblast growth factor-fibrin complex: in vitro and in vivo applications to collagen-based materials", *Biomaterials.*, 15(9):665-72 (1994).

Dedhar and Hannigan, "Integrin cytoplasmic interactions and bidirectional transmembrane signaling", Current Opinion in Cell Biology, 8:657-669 (1996).

Dimilla, et al., "Mathematical model for the effects of adhesion and mechanics on cell migration speed", Biophys. J., 60(1):15-37 (1991).

Dinbergs, et al., "Cellular response to transforming growth factor-beta1 and basic fibroblast growth factor depends on release kinetics and extracellular matrix interactions", *J. Biol. Chem.*, 271(47):29822-9 (1996).

Downs, et al., "Calcium alginate beads as a slow-release system for delivering angiogenic molecules in vivo and in vitro", *Journal of Cellular Physiology*, 152:422-429 (1992).

Edelman, et al., "Basic fibroblast growth factor enhances the coupling of intimal hyperplasia and proliferation of vasa vasorum in injured rat arteries", *J. Clin. Invest.*, 89(2):465-73 (1992).

Edelman, et al., "Controlled and modulated release of basic fibroblast growth factor", *Biomaterials.*, 12(7):619-26 (1991).

Edelman, et al., "Perivascular and intravenous administration of basic fibroblast growth factor: vascular and solid organ deposition", *Proc. Natl. Acad. Sci. U. S. A.*, 90(4):1513-7 (1993).

Edgar, et al., "The heparin-binding domain of laminin is responsible for its effects on neurite outgrowth and neuronal survival", *EMBO J.*, 3(7):1463-8 (1984).

Eliceiri and Cheresh, "The role of alphav integrins during angiogenesis: insights into potential mechanisms of action and clinical development", *Journal of Clinical Investigation*, 103:1227-1230 (1999).

Esposito and Caputo, "Mammalian transglutaminases. Identification of substrates as a key to physiological function and physiopathological relevance", *FEBS J.*, 272(3):615-31 (2005).

Fasol, et al., "Experimental use of a modified fibrin glue to induce site-directed angiogenesis from the aorta to the heart", *Journal of Thoracic and Cardiovascular Surgery*, 107:1432-9 (1994).

Felding-Habermann, et al., "A single immunoglobulin-like domain of the human neural cell adhesion molecule L1 supports adhesion by multiple and platelet integrins", *J Cell Biol*, 139:1567-1581 (1997).

Feng, et al., "Roles for ephrins in positionally selective synaptogenesis between motor neurons and muscle fibers", *Neuron*, 25:295-306 (2000).

Ferrara and Alitalo, "Clinical applications of angiogenic growth factors and their inhibitors", *Nature Medicine*, 5:1359-1364 (1999).

Ferrara, "Molecular and biological properties of vascular endothelial growth factor", *J Mol Med*, 77:527-543 (1999).

Folkman, "Angiogenesis in cancer, vascular, rheumatoid and other disease", *Nature Medicine*, 1:27-31 (1995).

Gale, et al., "Ephrin-B2 selectivity marks arterial vessels and neovascularization sites in the adult, with expression in both endothelial and smooth-muscle cells", *Developmental Biology*, 230:151-160 (2001).

Giannelli, et al., "Transforming growth factor-beta1 triggers hepatocellular carcinoma invasiveness via alpha3beta1 integrin", *Am J Pathol.*, 161(1):183-93 (2002).

Gittens, et al. "Designing Proteins for Bone Targeting", *Advanced Drug Delivery Reviews* 57(7):1-11-1036(2005).

Götz, et al., "Neurotrophin-6 is a new member of the nerve growth factor family", *Nature*, 372(6503):266-9 (1994).

Grainger, et al., "Poly(dimethylsiloxane)-poly(ethylene oxide)-heparin block copolymers. I. Synthesis and characterization", *J. Biomed Mater Res.*, 22(3): 231-249 (1988).

Gram, et al., "A novel approach for high level production of a recombinant human parathyroid hormone fragment in *Escherichia coli*", *Biotechnology* (N Y), 12(10):1017-23 (1994) (abstract only).

Griesler, et al., "Enhanced endothelial of expanded polyethrafluoroethylene grafts by fibroblast growth factor type 1 pretreatment", Surgery, 112:244-255 (1992).

Groenen, et al., "The carboxy-terminal lysine of alpha B-crystallin is an amine-donor substrate for tissue transglutaminase", Eur J Biochem., 205(2):671-4 (1992).

Grootjans, et al., "Substrate requirements for transglutaminases. Influence of the amino acid residue preceding the amine donor lysine in a native protein", *J Biol Chem.*, 270(39):22855-8 (1995).

Gupta, et al., "Arterial vimentin is a transglutaminase substrate: a link between vasomotor activity and remodeling?", *J. Vas. Res.*, 44(5):339-344 (2007).

Hall, "Molecular properties of fibrin-based matrices for promotion of angiogenesis in vitro", *Microvascular Research*, 62:315-326 (2001).

Hall, et al., "Trimerization of cell adhesion molecule L1 mimics clustered L1 expression on the cell surface: Influence on L1-Ligand interactions and on promotion of neurite outgrowth", *J of Neurochemistry*, 75:336-346 (2000).

Hammoud, et al., "Management of coronary artery disease: Therapeutic options in patients with diabetes", *J Am. Col. Cardiology*, 36:355-65 (2000).

Harada, et al., "Basic fibroblast growth factor improves myocardial function in chronically ischemic porcine hearts", *J. Clin. Invest.*, 94(2):623-30 (1994).

Hata, et al., "Binding of lipoprotein lipase to heparin. Identification of five critical residues in two distinct segments of the amino-terminal domain", *J. Biol. Chem.*, 268(12):8447-57 (1993).

Haugen, et al, "Central and peripheral neurite outgrowth differs in preference for heparin-binding versus integrin-binding sequences", *J. Neurosci.*, 12(6):2034-42 (1992).

Herbert, et al., "Effects of fibinolysis on neurite growth from dorsal root ganglia cultured in two- and three-dimensional fibrin gels", *J. Comp. Neurol.*, 365(3):380-91 (1996).

Herbert, et al., "Effects of fibrin micromorphology on neurite growth fro m dorsal root ganglia cultured in three-dimensional fibrin gels", *J. Biomed. Mat. Res.*, 40(4):551-9 (1998).

Hern, et al., "Incorporation of adhesion peptides into nonadhesive hydrogels useful for tissue resurfacing", *J. Biomed Mater. Res.*, 39:266-276 (1998).

Hettasch, et al., "Analysis of factor XIII substrate specificity using recombinant human factor XIII and tissue transglutaminase chimeras", *J Biol Chem.*, 272(40): 25149-25156 (1997).

Hildebrand, et. al., "The effects of platelet-derived growth factor-BB on healing of the rabbit medial collateral ligament. An in vivo study", *Am J Sports Med* 26(4): 549-554 (1998).

Hoppe, et al., "Preparation of biologically active platelet-derived growth factor type BB from a fusion protein expressed in *Escherichia coli*", Biochemistry 28(7): 2956-2960 (1989).

Hoppe, et al., "Preparation of biologically active platelet-derived growth factor isoforms AA and AB. Preferential formation of AB heterodimers", *Eur J Biochem* 187(1): 207-214 (1990).

Houle & Johnson, "Nerve growth factor (NGF)-treated nitrocellulose enhances and directs the regeneration of adult rat dorsal root axons through intraspinal neural tissue transplants", *Neuroscience Letters*, 103:17-23 (1989).

Hubbell, "Bioactive biomaterials", *Curr. Opinion Biotechnol.*, 10(2):123-129 (1999).

Humphries, "Integrin activation: the link between ligand binding and signal transduction", *Curr Opin Cell Biol*, 8:632-640 (1996).

Ilan, et al., "Distinct signal transduction pathways are utilized during the tube formation and survival phases of in vitro angiogenesis", *J of Cell Science*, 111:3621-3631 (1998).

Ingber and Folkman, "How does extracellular matrix control capillary morphogenesis?", *Cell*, 58:803-805 (1989).

Isaacs, "Cystine knots", *Curr. Opin. Struct. Biol.*, 5(3):391-5 (1995).

Jagur-Grodzinski, et al. "Biomedical application of functional polymers", *Reactive Polymers* 39(2):99-138(1999).

Jeong, et al., "The fibronectin-binding domain of transglutaminase", *J Biol Chem.*, 270(10):5654-8 (1995).

Jin et. al., "Effects of geometry of hydroxyapatite as a cell substratum in BMP-induced ectopic bone formation", *J Biomed Mat Res* 52, 491-499 (2000).

Kahlem, et al., "Peptides containing glutamine repeats as substrates for transglutaminase-catalyzed cross-linking: relevance to diseases of the nervous system", *Proc. Natl. Acad. Sci. USA*, 93(25):14580-14585 (1996).

Kallapur, et al, "The neural cell adhesion molecule (NCAM) heparin binding domain binds to cell surface heparan sulfate proteoglycans", *J. Neuro. Res.*, 33(4):538-48 (1992).

Kaneda, et al., "Midkine, a heparin-binding growth/differentiation factor, exhibits nerve cell adhesion and guidance activity for neurite outgrowth in vitro", *J. Biochem.*, 119(6):1150-6 (1996).

Kang, et al., "Selective stimulation of endothelial cell proliferation with inhibition of smooth muscle cell proliferation by fibroblast growth factor-1 plus heparin delivered from glue suspensions", *Surgery*, 118:280-287 (1995).

Keyt, et al., "The carboxyl-terminal domain (111-165) of vascular endothelial growth factor is critical for its mitogenic potency", *J. Biol. Chem.*, 271(13):7788-95 (1996).

Kiguchi, et al., "Altered expression of epidermal growth factor receptor ligands in tumor promoter-treated mouse epidermis and in primary mouse skin tumors induced by an initiation-promotion protocol", *Mol. Carcinog.*, 22(2):73-83 (1998).

Kinosaki, et al., "Identification of heparin-binding stretches of a naturally occurring deleted variant of hepatocyte growth factor (dHGF)", *Biochim. Biophys. Acta.*, 1384(1):93-102 (1998).

Kleinman, et al., "The laminins: a family of basement membrane glycoproteins important in cell differentiation and tumor metastases", *Vitam. Horm.*, 47:161-86 (1993).

Lasa, et al., "Delivery of demineralized bone powder by fibrin sealant", *Plast. Reconstr. Surg.* 96(6):1409-17 (1995).

Lee, et al., "Analysis of affinity and structural selectivity in the binding of proteins to glycosaminoglycans: Development of a sensitive electrophoretic approach", *Biochemistry*, 88:2768-2772 (1991).

Li (ed), *Hormonal Proteins and Peptides*, vol. 7, Academic Press, Inc: New York, pp. 231-277.

Lin, et al., "Purification and initial characterization of rat B49 glial cell line-derived neurotrophic factor", *Journal of Neurochemistry*, 63(2):758-768 (1994).

Lopez, et al., "Basic fibroblast growth factor in a porcine model of chronic myocardial ischemia: a comparison of angiographic, echocardiographic and coronary flow parameters", *J. Pharmacol. Exp. Ther.*, 282(1):385-90 (1997).

Lopez, et al., "Local perivascular administration of basic fibroblast growth factor: drug delivery and toxicological evaluation", *Drug Metab. Dispos.*, 24(8):922-4 (1996).

Lorsordo, et al., "Gene therapy for myocardial angiogenesis. Initial clinical results with direct myocardial injection of phVEGF165 as sole therapy for myocardial ischemia", *Circulation*, 98:2800-2804 (1998).

Ludbrook, et al., "The integrin alphavbeta3 is a receptor for the latency-associated peptides of transforming growth factors beta1 and beta3", *Biochem J.*, 369(Pt 2):311-8 (2003).

Luginbuehl, et al. "Localized delivery of growth factors for bone repair", *Eur. J. of Pharm. And Biopharm.* 58(2):197-208(2004).

Lyon, et al., "The interaction of the transforming growth factor-βs with heparin/heparan sulfate is isoform-specific", *The Journal of Biological Chemistry*, 272(29):18000-18006 (1997).

Martin and Timpl, "Laminin and other basement membrane components", *Annu. Rev. Cell.Dev. Biol.*, 3:57-85 (1987).

Massia, et al., "An RGD spacing of 440 nm is sufficient for integrin alpha V beta 3-mediated fibroblast spreading and 140 nm for focal contact and stress fiber formation", *J. Cell. Biol.*, 114(5):1089-100 (1991).

Maysinger, et al., "Microencapsulated nerve growth factor: effects on the forebrain neurons following devascularizing cortical lesions", *Neuroscience Letters*, 140:71-74 (1992).

McCaffrey, et al., "Transforming growth factor-beta 1 is a heparin-binding protein: identification of putative heparin-binding regions and isolation of heparins with varying affinity for TGF-beta 1", *J. Cell. Physiol.*, 152(2):430-40 (1992).

Mergulhao, et al., "Troubleshooting in gene splicing by overlap extension: a step-wise method", *Mol. Biotechnol.*, 12(3):285-7 (1999).

Miyazono, et al., "Divergence and convergence of TGF-beta/BMP signaling", *J. Cell Physiol.*, 187(3):265-76 (2001).

Monsonego, et al., "Factor XIIIa as a nerve-associated transglutaminase", *FASEB J.*, 12(12):1163-71 (1998).

Montgomery, et al., "Human neural cell adhesion molecule L1 and rat homologue NILE are ligands for integrin alpha v beta 3", *J Cell Biol*, 132:475-485 (1996).

Mosher, et al., "Cross-linking of collagen and fibronectin by factor XIIIa. Localization of participating glutaminyl residues to a tryptic fragment of fibronectin", *J. Biol. Chem.*, 255(3):1181-8 (1980).

Nakagawa, et al., "Production of human PTH(1-34) via a recombinant DNA technique", *Biochem. Biophys. Res. Commun.*, 200(3):1735-41 (1994).

Nehls and Herrmann, "The configuration of fibrin clots determine capillary morphogenesis and endothelial cell migration", *Microvascular Research*, 51:347-364 (1996).

Nesti, et al., "TGF-beta1 calcium signaling increases alpha5 integrin expression in osteoblasts", *J Orthop Res.*, 20(5):1042-9 (2002).

Netzel-Arnett, et al., "Sequence specificities of human fibroblast and neutrophil collagenases", *J. Biol. Chem.*, 266:6747-6755 (1991).

Nolo, et al., "Developmentally regulated neurite outgrowth response from dorsal root ganglion neurons to heparin-binding growth-associated molecule (HB-GAM) and the expression of HB-GAM in the targets of the developing dorsal root ganglion neurites", *Eur. J. Neurosci.*, 8(8):1658-65 (1996).

Pacioreck, et al. *Annual fall meeting of the BMES*, poster abstract P2.199 (Sep. 26-29, 2007).

Pandit, et al., "Fibrin scaffold as an effective vehicle for the delivery of acidic fibroblast growth factor (FGF-1)", *J Biomater Appl* 14(3): 229-242 (2000).

Pepper, et al., "Angiogenesis: a paradigm for balanced extracellular proteolysis cell migration and morphogenesis", *Enzyme Protein*, 49:138-162 (1996).

Pineda-Lucena, et al., "Three-dimensional structure of acidic fibroblast growth factor in solution: effects of binding to a heparin functional analog", *J Mol Biol* 264(1): 162-178 (1996).

Pisano, et al., "Cross-link in fibrin polymerized by factor 13: epsilon-(gamma-glutamyl)lysine", *Science* 160(3830): 892-893 (1968).

Pittman, et al., "Degradation of extracellular matrix by neuronal proteases", *Dev Neuro* 11(4-5): 361-375 (1989).

Potts, "Parathyroid hormone: past and present", *J Endocrinol.*, 187(3):311-25 (2005).

Powell, et al., "Controlled release of nerve growth factor from a polymeric implant", *Brain Research* 515:309-311 (1990).

Presta, et al., "Structure-function relationship of basic fibroblast growth factor: site-directed mutagenesis of a putative heparin-binding and receptor-binding region", *Biochem. Biophys. Res. Commun.*, 185(3):1098-107 (1992).

Quirinia, et al., "The effect of recombinant basic fibroblast growth factor (bFGF) in fibrin adhesive vehicle on the healing of ischaemic and normal incisional skin wounds", *Scand J Plast Reconstr Surg Hand Surg* 32(1): 9-18 (1998).

Rajan, et al., "Characterization of recombinant human interleukin 4 receptor from CHO cells: role of N-linked oligosaccharides", *Biochem Biophys Res Commun* 206(2): 694-702 (1995).

Reddi, "Role of morphogenetic proteins in skeletal tissue engineering and regeneration", *Nature Biotechnol.*, 16:247-252 (1998).

Rixon, et al., "Do the non-catalytic polysaccharide-binding domains and linker regions enhance the biobleaching properties of modular xylanases?", *Appl. Microbiol. Biotechnol.*, 46(5-6): 514-520 (1996).

Rixon, et al., "Parathyroid hormone fragments may stimulate bone growth in ovariectomized rats by activating adenylyl cyclase", *J Bone Miner. Res.*, 9(8):1179-89 (1994).

Robello, et al., "Delayed and nonunion fractures", *Semin Vet Med Surg (Small Anim)* 7(1): 98-104 (1992).

Rogers, et al., "Neuron-specific interactions with two neurite-promoting fragments of fibronectin", *J. Neurosci.*, 5(2):369-78 (1985).

Rosengart, et al., "Angiogenesis Gene Therapy. Phase I assessment of direct intramyocardial administration of an adenovirus expressing phVEGF165 cDNA to individuals with clinically significant severe coronary artery disease", *Circulation*, 100:468-474 (1999).

Rout, et al., "Transforming growth factor-beta 1 modulates expression of adhesion and cytoskeletal proteins in human peritoneal fibroblasts", *Fertil Steril.*, 78(1):154-61 (2002).

Ruoslahti and Engvall, "Perspectives series: Cell adhesion in vascular biology", *J Clin Invest*, 99:1149-1152 (1997).

Sakata & Aoki, et al., "Cross-linking of alpha 2-plasmin inhibitor to fibrin by fibrin-stabilizing factor", *J Clin Invest*, 65:290-297 (1980).

Sakiyama, et al., "Incorporation of heparin-binding peptides into fibrin gels enhances neurite extension: an example of designer matrices in tissue engineering", *FASEB J* 13(15): 2214-24 (1999).

Sakiyama-Elbert and Hubbell, "Controlled release of nerve growth factor from a heparin-containing fibrin-based cell ingrowth matrix", *Journal of Controlled Release*, 69:149-158 (2000).

Sakiyama-Elbert, et al., "Development of fibrin derivatives for controlled release of heparin binding growth factors", J. Controlled Release, 65(3) 389-402 (2000).

Sakiyama-Elbert, et al., "Development of growth factor fusion proteins for cell-triggered drug delivery", *FASEB J.*, 15:1300-1302 (2001).

Sampath, et al., "Bovine osteogenic protein is composed of dimers of OP-1 and BMP-2A, two members of the transforming growth factor-beta superfamily", *J. Biol. Chem.*, 265(22):13198-205 (1990).

Saraph, et al., "Treatment of unicameral calcaneal bone cysts in children: review of literature and results using a cannulated screw for continuous decompression of the cyst", *J. Pediatr. Orthop.*, 24(5):568-73 (2004).

Saunders, et al., "Optimization of the signal-sequence cleavage site for secretion from Bacillus subtilis of a 34-amino acid fragment of human parathyroid hormone", *Gene* 102(2):277-82 (1991) (abstract only).

Sawhney, et al., "Bioerodible hydrogels based on photopolymerized poly(ethylene glycol)-co-poly(.alpha.-hydroxy acid) diacrylate macromers", Macromolecules, 26(4): 581-587 (1993).

Schense, et al., "Cross-linking exogenous bifunctional peptides into fibrin gels with factor XIIIa,", *Bioconjug. Chem.*, 10(1): 75-81 (1999).

Schense, et al., "Enzymatic incorporation of bioactive peptides into fibrin matrices enhances neurite extension", *Nature Biotechnology*, 18:415-419 (2000).

Schmitz, et al., "The critical size defect as an experimental model for craniomandibulofacial nonunions", *Clin Orthop*, 205: 299-308 (1986).

Schmoekel, et al., "Bone repair with a form of BMP-2 engineered for incorporation into fibrin cell ingrowth matrices", *Biotechn. Bioengin.* 89(3): 253-262 (2005). Epud. Dec. 2004.

Schroeder-Tefft, et al., "Collagen and heparin matrices for growth factor delivery", Journal of Controlled Release, 49:291-298 (1997).

Schumacher, et al., "Induction of neoangiogenesis in ischemic myocardium by human growth factors", Circulation, 97:645-650 (1998).

Seibel, et al., Transfection of mitochnondria: strategy towards a gene therapy of mitochondrial DNA diseases, *Nucleic Acids Res.*, 23(1): 10-7 (1995).

Sellke, et al., "Basic FGF enhances endothelium-dependent relaxation of the collateral-perfused coronary microcirculation", *Am. J. Physiol.* 267(4 Pt 2):H1303-11 (1994).

Shin, et al., "Expression of EphrinB2 identifies a stable genetic difference between arterial and venous vascular smooth muscle as well as endothelial cells, and of adult neovascularization", *Developmental Biology*, 230:139-150 (2001).

Shireman, et al., "Modulation of vascular cell growth by local cytokine delivery from fibrin glue suspendions", *J Vasc Surg*, 19:852-62 (1999).

Sierra, "Fibrin sealant adhesive systems: a review of their chemistry, material properties and clinical applications", *J Biomater Appl* 7(4): 309-352 (1993).

Skripitz, et al., "Strong effect of PTH (1-34) on regenerating bone: a time sequence study in rats", *Acta. Orthop. Scand.*, 71(6):619-24 (2000).

Smith, et al., "Rapid identification of highly active and selective substrates for stromelysin and matrilysin using bacteriophage peptide display libraries", *J. Biol. Chem.*, 270:6440-6449 (1995).

Spillman, et al., "Defining the interleukin-8-binding domain of heparan sulfate", *J. Biol. Chem.*, 273(25):15487-93 (1998).

Steffen, et al., "Characterization of cell-associated and soluble forms of connective tissue growth factor (CTGF) produced by fibroblast cells in vitro", *Growth Factors*, 15(3):199-213 (1998).

Stein, et al., "Eph receptors discriminate specific ligand oligomers to determine alternative signaling complexes, attachment, and assembly responses", *Genes & Development*, 12:667-678 (1998).

Studier, et al., "Use of T7 RNA polymerase to direct expression of cloned genes", *Methods Enzymol.* 185:60-89 (1990).

Takagi and Doolittle, "Amino acid sequence studies on the alpha chain of human fibrinogen. Location of four plasmin attack points and a covalent cross-linking site", *Biochem.*, 14:5149-5156 (1975).

Takeshita, et al., "Therapeutic angiogenesis. A single intraarterial bolus of vascular endothelial growth factor augments revascularization in a rabbit ischemic hind limb model", *J Clin Invest*, 93:662-670 (1994).

Tamaki, et al., "Cross-linking of alpha 2-plasmin inhibitor to fibrin catalyzed by activated fibrin-stabilizing factor", *J Biol Chem* 257(24): 14767-14772 (1982).

Tams, et al., "Adapting protein solubility by glycosylation. N-glycosylation mutants of Coprinus cinereus peroxidase in salt and organic solutions", *Biochem Biophys Acta* 1432(2): 214-221 (1999).

Tashiro, et al., "A synthetic peptide containing the IKVAV sequence from the A chain of laminin mediates cell attachment, migration, and neurite outgrowth", *J. Biol. Chem.*, 264(27):16174-82 (1989).

Tessler, et al., "Heparin modulates the interaction of VEGF165 with soluble and cell associated flk-1 receptors", *J. Biol. Chem.*, 269(17):12456-61 (1994).

TGF-beta Superfamily Ligands, retrieved from www.rndsystems. com/molecule_group.aspx?g=480&r=1 on Jul. 13, 2007.

Thompson, et al., "Site-directed neovessel formation in vivo", *Science*, 241:1349-1352 (1988).

Tsutsumi, et al., "Chemical modification of natural human tumor necrosis factor-alpha with polyethylene glycol increases its anti-tumor potency", *Japanese Journal of Cancer Research*, 85(1):9-12 (1994).

Tyler-Cross, et al., "Heparin binding domain peptides of antithrombin III: analysis by isothermal titration calorimetry and circular dichroism spectroscopy", *Protein Sci.*, 3(4):620-7 (1994).

Urist, et al., "Solubilized and insolubilized bone morphogenetic protein", *Proc Natl Acad Sci U.S.A.* 76(4): 1828-1832 (1979).

Usui, et al., "Propolypeptide of von Willebrand factor serves as a substrate for factor XIIIa and is cross-linked to laminin", *J Biol Chem.*, 268(17):12311-6 (1993).

Van Brunt and Klausner, "Growth factors speed wound healing", *Nature Biotechnology*, 6: 25-30 (1988).

Wang, et al., "Molecular distinction and angiogenesis interaction between embryonic arteries and veins revealed by ephrin-B2 and its receptor Eph-B4", *Cell*, 93:741-753 (1998).

Weatherford, et al., "Vascular endothelial growth factor and heparin in a biologic glue promotes human aortic endothelial cell proliferation with aortic smooth muscle cell inhibition", *Surgery*, 433-439 (1996).

Wells, "Additivity of mutational effects in proteins", *Biochemistry*, 29(37):8509-8517 (1990).

Wozney, "Bone morphogenetic proteins", *Prog Growth Factor Res* 1(4): 267-280 (1989).

Wozney, et al., "Growth factors influencing bone development", *J Cell Sci Suppl* 13: 149-156 (1990).

Yamada, "Adhesive recognition sequences", *J. Biol. Chem.*, 266(20):12809-12 (1991).

Yamada, et al., "Characterization of fibronectin interactions with glycosaminoglycans and identification of active proteolytic fragments", *J Biol Chem.*, 255(13):6055-63 (1980).

Yanish-Perron, et al., "Improved M13 phage cloning vectors and host strains: nucleotide sequences of the M13mp18 and pUC19 vectors", *Gene*, 33(1):103-19 (1985).

Zisch, et al., "Covalently conjugated VEGF-fibrin matrices for endothelialization", *Journal of Controlled Release*, 72:101-113 (2001).

Zucker and Katz, "Platelet factor 4: production, structure, and physiologic and immunologic action", *Proc. Soc. Exp. Biol. Med.*, 198(2):693-702 (1991).

* cited by examiner

US 8,226,942 B2

PDGF FUSION PROTEINS INCORPORATED INTO FIBRIN FOAMS

CROSS REFERENCE TO RELATED APPLICATION

This application is a continuation of PCT/EP2008/068185 filed on Dec. 22, 2008, which claims priority to U.S. Provisional Application No. 61/017,409, filed on Dec. 28, 2007; this application also claims priority to and benefit of U.S. Provisional Application No. 61/017,409, filed on Dec. 28, 2007.

FIELD OF THE INVENTION

The present invention generally relates to compositions, kits and methods for forming fibrin matrices or foams including fusion proteins. A preferred fusion protein is a platelet derived growth actor comprising a transglutaminase substrate domain which enables the covalently linked to the matrix. The fibrin matrices enable for controlled release of the growth factor for tissue repair or regeneration and in particular for wound healing. In particular, the present invention relates to methods for forming supplemented fibrin foams.

BACKGROUND OF THE INVENTION

For tissue repair or regeneration, cells must migrate into a wound bed, proliferate, express matrix components or form extracellular matrix, and form a final tissue shape. Multiple cell populations must often participate in this morphogenetic response, frequently including vascular and nerve cells. Matrices have been demonstrated to greatly enhance, and in some cases have been found to be essential, for this to occur. Natural cell in-growth matrices are subject to remodeling by cellular influences, all based on proteolysis, e.g., by plasmin (degrading fibrin) and matrix metalloproteinases (degrading collagen, elastin, etc.). Such degradation is highly localized, and only upon direct contact with the cell. In addition, the delivery of specific cell signaling proteins, such as growth factors, is tightly regulated.

When a tissue is injured, polypeptide growth factors which exhibit an array of biological activities are released into the wound where they play a crucial role in healing (see, e.g., Hormonal Proteins and Peptides, Li, C. H., ed., Volume 7, Academic Press, Inc. New York, pp. 231-277 and Brunt et al., Biotechnology 6:25-30 (1988)). These activities include, recruiting cells, such as leukocytes and fibroblasts, into the injured area, and inducing cell proliferation and differentiation. Growth factors that participate in wound healing include: platelet-derived growth factor (PDGF), insulin-binding growth factor-1 (IGF-1), insulin-binding growth factor-2 (IGF-2), epidermal growth factor (EGF), transforming growth factors (TGF-α), transforming growth factor-β (TGF-β), platelet factor 4 (PF-4), and heparin binding growth factors one and two (HBGF-1 and HBGF-2).

Fibrin is a natural material which has been reported for several biomedical applications. Fibrin gels have been used as sealants due to their ability to adhere to many tissues and their natural role in wound healing. Some specific applications include use as a sealant for vascular graft attachment, heart valve attachment, bone positioning in fractures and tendon repair. Additionally, these gels have been used as drug delivery devices, and for neuronal regeneration as well as material for cell in-growth matrices (U.S. Pat. No. 6,331,422 to Hubbell et al.).

The incorporation of bioactive factors in natural or synthetic biomaterials or mixtures thereof are mainly done by incorporation of the bioactive factor through physical interaction as has been described, for example, in U.S. Pat. Nos. 6,117,425 and 6,197,325 and WO02/085422. Covalent linking of the bioactive factor to the biomaterial is a more advanced technique allowing improved control of the release profile of the bioactive factor from the biomaterial. The incorporation of small synthetic or naturally occurring molecules, peptides and/or proteins into fibrin matrices through action of transglutaminases has been described in U.S. Pat. Nos. 6,331,422; 6,468,731 and 6,960,452 and WO 03/052091 and Schense, J. C., et al. (1999) Bioconj. Chem. 10:75-81. Covalent cross-linking of the bioactive factor may be performed by modifying the bioactive factor through incorporation of functional groups, which are able to react with one or more of the reactive groups of the precursor components or biomaterials during or after formation of the biomaterial. U.S. patent application No 2003/0187232 discloses a fibrin gel supplemented with a PDGF modified with transglutaminase substrate domain and its use in chronic wound healing in human patients. However, with the system describes therein, a high amount of growth factor is released from the fibrin gel in the first hours after application.

While delivery systems for proteins and growth factors are known, there remains a need for controlling the amount of growth factor released over time as well as the rate of release of the growth factor. In particular, there is a need to reduce the amount of growth factor to be released in the first hours following application It is therefore an object of the present invention to provide fibrin matrices for enhanced controlled and/or sustained release of growth factors.

It is a further object of the present invention to provide methods for the formation of a fibrin matrix supplemented by growth factors.

It is a further object of the present invention to provide compositions and methods for the formation of a fibrin foam supplemented with growth factors.

It is a further object of the present invention to provide methods for the formation of a fibrin foam supplemented by growth factors.

SUMMARY OF THE INVENTION

Compositions for wound healing, use of the compositions, and kits and methods of using thereof are described herein.

In one aspect, the compositions are suitable for forming fibrin matrices with enhanced controlled release of the growth factor incorporated therein.

In a preferred aspect, the compositions are suitable for use in a method for forming a fibrin foam that can be applied at the site of need before complete crosslinking had occurred.

In another preferred aspect, the compositions are also suitable for use in methods for forming controlled delivery fibrin matrices that can be administered as foams.

Foamed fibrin matrices are provided that are biodegradable, porous and have fusion proteins incorporated into the matrix in such a way that the protein is covalently linked to the matrix, retains its biological activity and is slowly released in the first hours following application.

In one aspect, the invention provides a composition including:
(i) fibrinogen;
(ii) thrombin wherein the amount of thrombin is less than 0.3 UI of thrombin/mg of fibrinogen; and (iii) at least one fusion protein comprising a first domain comprising a PDGF and a second domain comprising a transglutaminase substrate domain. The composition can further comprise a calcium source.

In one embodiment, the second domain of the fusion protein includes a transglutaminase substrate domain (TG) which has a Factor XIIIa substrate domain. Preferably, the Factor XIIIa substrate domain comprises SEQ ID NO:1.

In another embodiment, the fusion protein further includes a degradation site between the first and the second domain of the fusion protein. In a preferred embodiment, the degradation site is an enzymatic or hydrolytic degradation site. In a most preferred embodiment, the degradation site is an enzymatic degradation site, which is cleaved by an enzyme selected from the group consisting of plasmin and matrix metalloproteinase.

In a most preferred embodiment, the fusion protein comprises an amino acid sequence of SEQ ID NO:2 and SEQ ID NO:3.

In another embodiment, the concentration of the fibrinogen solution is in a range of about 10 mg/ml to 130 mg/ml, preferably about 50 mg/ml of the fibrinogen precursor solution In a preferred embodiment, the thrombin amount is from about 0.04 to 0.28 I.U. thrombin per mg of fibrinogen, preferably about 0.08 I.U. thrombin per mg of fibrinogen.

In another embodiment, the fusion protein is in an amount in a range from about 1 to 20 µg/mg of fibrinogen, preferably from about 1.32 to 16 µg/mg of fibrinogen and most preferably from 4 to 12 µg/mg of fibrinogen.

In her aspect, the invention provides a kit including
(i) a first container comprising fibrinogen and at least one fusion protein, comprising a first domain comprising a PDGF and a second domain comprising a substrate domain for a crosslinking enzyme; and
(ii) a second container comprising thrombin, wherein the amount of thrombin is less than 0.3 U.I. thrombin per mg of fibrinogen; and a calcium source.

The kit of the present invention can further comprise a biocompatible gas selected from the group consisting of $CO_2$, $N_2$, air or an inert gas, preferably air. The biocompatible gas is either in the first or the second container.

In a further aspect, the present invention provides a method for preparing a fibrin matrix having at least one fusion protein, the method including the steps of:
(i) providing a fibrinogen solution;
(ii) providing a thrombin solution wherein the amount of thrombin is less than 0.3 I.U. thrombin per mg of fibrinogen;
(iii) providing at least one fusion protein comprising a first domain comprising a PDGF and a second domain comprising a transglutaminase substrate domain; and
(iv) mixing components provided in steps (i), (ii) and (iii) to crosslink the matrix material such that the fusion protein is covalently linked to the matrix through the second domain.

In order to form a fibrin foam, components provided in steps (i), (ii) and (iii) are mixed with a biocompatible gas selected from the group consisting of $CO_2$, $N_2$, air or an inert gas, preferably air to crosslink the foam material such that the fusion protein is covalently linked to the matrix through the second domain.

In a preferred embodiment, the volume of the fibrinogen solution is from about 40 to 60% of the volume of the biocompatible gas, preferably about 50% of the volume of the biocompatible gas.

A further aspect provides a controlled delivery fibrin matrix obtained according to the disclosed method. Preferably, the controlled delivery fibrin matrices are characterized in that no more than 25% of the growth factor is released after incubation of the controlled delivery fibrin matrix during 3 days at 37° C. in a buffer solution.

Still another embodiment provides a controlled delivery fibrin foam obtained according to the disclosed methods. Preferably, no more than 25% of the growth factor is released after incubation of the controlled delivery fibrin matrix for 3 days at 37° C. in a buffer solution.

Another aspect provides a fibrin foam including:
(i) fibrinogen;
(ii) thrombin wherein the amount of thrombin is less than 0.3 I.U. of thrombin/mg of fibrinogen; and
(iii) at least one fusion protein comprising a first domain comprising a PDGF and a second domain comprising a transglutaminase substrate domain, and
(iv) a biocompatible gas selected from the group consisting of $CO_2$, $N_2$, air or an inert gas, preferably air.

Still another aspect provides a method for preparing a fibrin foam supplemented with PDGF. The method includes the steps of:
(i) providing a fibrinogen solution
(ii) providing a thrombin solution wherein the amount of thrombin is less than 0.3 I.U. thrombin per mg of fibrinogen;
(iii) providing at least one fusion protein comprising a first domain comprising a platelet derived growth factor (PDGF) and a second domain comprising a transglutaminase substrate domain;
(iv) providing a biocompatible gas and
(v) mixing components provided in steps (i), (ii), (iii) and (iv) to form a fibrin foam.

In one embodiment, the second domain of the fusion protein includes a transglutaminase substrate domain (TG) which has a Factor XIIIa substrate domain. Preferably, the Factor XIIIa substrate domain is or includes SEQ ID NO: 1.

In another embodiment, the fusion protein her includes a degradation site between the first and the second domain of the fusion protein. In a preferred embodiment, the degradation site is an enzymatic or hydrolytic degradation site. In a most preferred embodiment, the degradation site is an enzymatic degradation site, which is cleaved by an enzyme selected from the group consisting of plasmin and matrix metalloproteinase.

In another preferred embodiment, the fusion protein includes an amino acid sequence of SEQ ID NO:2 and SEQ ID NO:3.

In another embodiment, the biocompatible gas is selected from the group consisting of $CO_2$, $N_2$, air or an inert gas such as Freon and is preferably air.

In another embodiment, the concentration of the fibrinogen solution is in a range of about 10 mg/ml to 130 mg/ml, preferably about 50 mg/ml of the fibrinogen precursor solution.

In a preferred embodiment, the thrombin amount is from about 0.04 to 0.28 I.U. thrombin per mg of fibrinogen, preferably about 0.08 I.U. thrombin per mg of fibrinogen.

In another embodiment, the fusion protein is in an amount in a range from about 1 to 20 µg/mg of fibrinogen, preferably from about 1.32 to 16 µg/mg of fibrinogen and more preferably from about 4 to 12 µg/mg of fibrinogen.

In another embodiment, controlled delivery fibrin foams are obtained according to the methods of the present invention for preparing fibrin foams supplemented with PDGF.

In a preferred embodiment, no more than 25% of PDGF is released after incubation of the controlled delivery fibrin matrix during 3 days at 37° C. in a buffer solution. Preferably, the amount of the fusion protein incorporated in the controlled delivery foams of the present invention is in a range from about 0.015 mg/ml to about 1 mg/ml of fibrin foam.

Still other embodiments include:

controlled delivery matrices or foams for use as a medicament;

controlled delivery matrices or foams for use in treatment of a wound, preferably wherein the wound is an ulcer caused by diabetes;

the use of the controlled delivery matrices or foams o for the manufacture of a medicament for treatment of a wound, preferably wherein the wound is an ulcer caused by diabetes.

DETAILED DESCRIPTION OF THE INVENTION

I. Definitions

Figure 1:
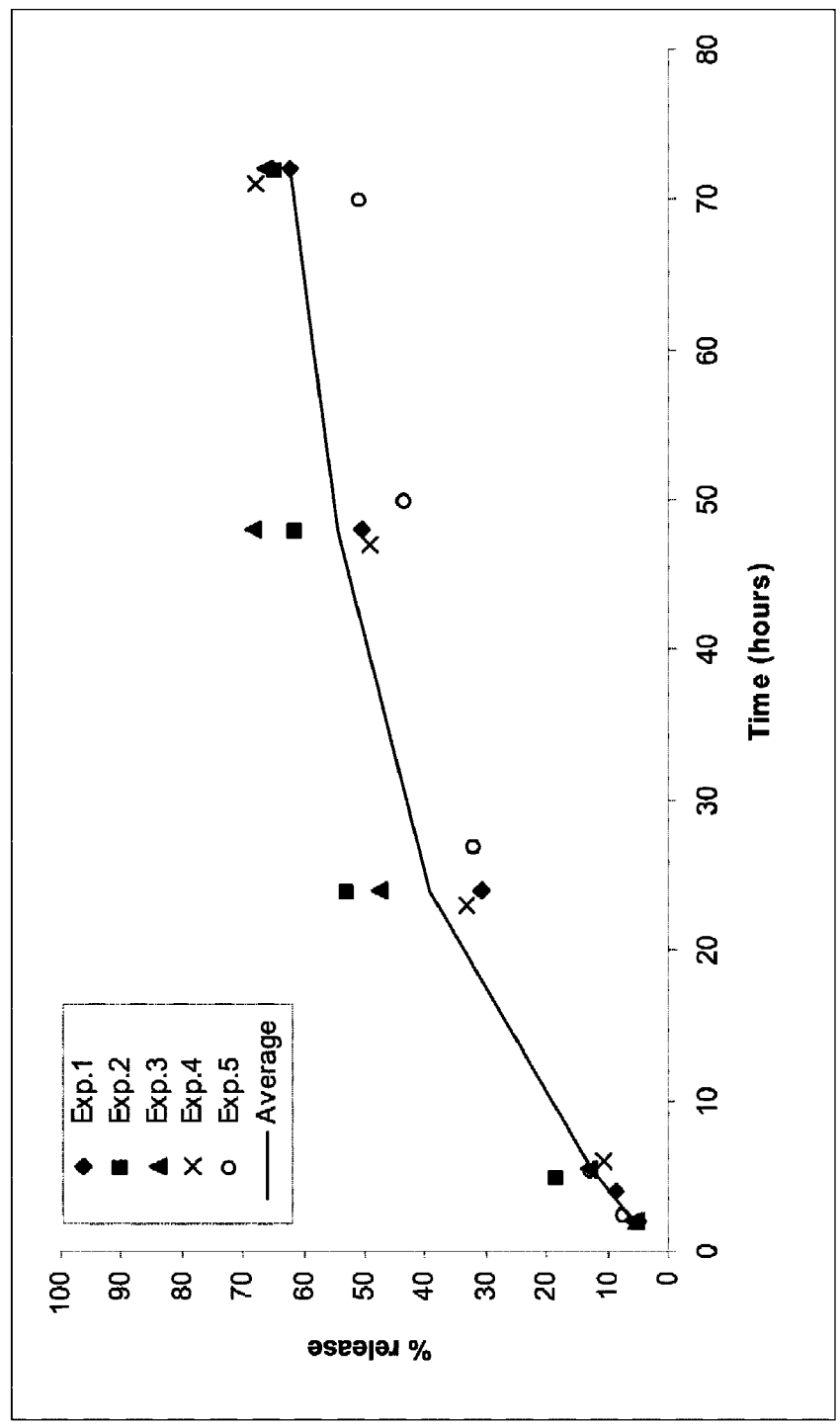
FIG. 1 is a line graph of the percent release of TG-PDGF.AB versus time (hours) from a fibrin matrix prepared with 50 mg/ml of fibrinogen, 250 I.U./ml of thrombin and 600 µg/ml of TG-PDGF.AB. Five experiments are plotted on the graph.

"Matrix" as generally used herein refers to a material intended to interface with biological systems to treat, augment, or replace any tissue or function of the tissue depending on the material either permanently or temporarily. The matrix can serve as a delivery device for drugs incorporated therein. The matrices described herein are formed from liquid precursor components which are able to form a three-dimensional network in the body at the site of need. The terms "matrix", "sealant" and "three-dimensional network" are used synonymously herein. The terms "matrix" and "seal ant" refer to the composition formed after the precursor solutions are mixed together and the crosslinking reaction has started. Thus the terms "matrix" and "sealant" encompass partially or fully crosslinked polymeric networks. They may be in the form of a semi-solid, such as a paste, a solid a gel or a foam. Depending on the type of precursor materials, the matrix may be swollen with water but not dissolved in water, i.e. form a hydrogel which stays in the body for a certain period of time.

"Foam" as generally used herein refers to a matrix having a biocompatible gas incorporated therein.

"Composition" as generally used herein refers to the precursors needed to form a fibrin matrix or a fibrin foam. The terms "composition" refer to the composition formed before the precursor solutions are mixed together and the crosslinking reaction has started.

"Fibrin Matrix" as generally used herein means the product of a process in which substantially all of the precursor components fibrinogen and thrombin crosslink in the presence of a calcium source, Factor XIIIa and excipients usually present in the precursor components to form a three-dimensional network.

"Fibrin Foam" as generally used herein means the product of a process in which substantially all of the precursor components fibrinogen and thrombin crosslink in the presence of a calcium source, Factor XIIIa and in the presence of a biocompatible gas and excipients usually present in the precursor components to form a three-dimensional network containing the biocompatible gas.

"Crosslinking" as generally used herein means the formation of covalent linkages.

"Supplemented matrix" as generally used herein refers to a matrix in which fusion proteins are releasably incorporated therein.

"Controlled release" or "controlled delivery" as used herein have the same meaning and refer to retention of an agent in the fibrin matrix or fibrin foam. The terms "controlled release" or "controlled delivery" mean that both the amount of the agent released over time and/or the rate of release of the agent are controlled.

II. Fibrin Matrices or Foams and Fusion Proteins

Fibrin matrices or foams containing fibrinogen, thrombin, and at least one fusion protein having a first domain that includes a growth factor and a second domain that includes a transglutaminase substrate domain are provided.

The fibrin matrices are prepared by combining a first solution, typically containing fibrinogen, a fusion protein, coagulation factor XIII substrate and coagulation factor XIIIa, and a second solution, typically containing thrombin and calcium chloride in an aqueous base. Fibrin foams are prepared by combining a biocompatible gas to a first solution, typically containing fibrinogen, a growth factor, a coagulation factor XIII substrate and a coagulation factor XIIIa, and a second solution, typically containing thrombin and calcium chloride in an aqueous base. In a preferred embodiment, the amount of thrombin is less than 0.3 U.I. thrombin per mg of fibrinogen.

A. Fibrin Matrix or Foam

Fibrin is a natural material which has been reported for several biomedical applications. Fibrin gels have been used as sealants due to their ability to bind to many tissues and their natural role in wound healing. Some specific applications include use as a sealant for vascular graft attachment, heart valve attachment, bone positioning in fractures and tendon repair. Additionally, these gels have been used as drug delivery devices, and for neuronal regeneration as well as material for cell in-growth matrices (U.S. Pat. No. 6,331,422 to Hubbell et al.).

The process by which fibrinogen is polymerized into fibrin has also been characterized. Initially, a protease cleaves the dimeric fibrinogen molecule at the two symmetric sites. There are several possible proteases than can cleave fibrinogen, including thrombin, peptidase, and protease III, and each one serves the protein at a different site. Once the fibrinogen is cleaved, a self-polymerization step occurs in which the fibrinogen monomers come together and form a non-covalently crosslinked polymer gel. This self-assembly happens because binding sites become exposed after protease cleavage occurs. Once they are exposed, these binding sites in the centre of the molecule can bind to other sites on the fibrinogen chains, which are present at the ends of the peptide chains. In this manner, a polymer network is formed. Factor XIIIa, a transglutaminase, activated from factor XIII by thrombin proteolysis, may then covalently crosslink to a polymeric network. Other transglutaminases exist and may also be involved in covalent crosslinking and grafting to the fibrin network.

Once a crosslinked fibrin gel is formed, the subsequent degradation is tightly controlled. One of the key molecules in controlling the degradation of fibrin is $\alpha 2$-plasmin inhibitor. This molecule acts by crosslinking to a chain of fibrin through the action of factor XIIIa. By attaching itself to the gel, a high concentration of inhibitor can be localized to the gel. The inhibitor then acts by preventing the binding of plasminogen to fibrin and inactivating plasmin. The $\alpha 2$-plasmin inhibitor contains a glutamine substrate.

In one embodiment, the composition capable of forming a fibrin matrix includes two precursor solutions in addition to at least one fusion protein.

In another embodiment, the composition capable of forming a fibrin foam includes two precursor solutions, at least one fusion protein and a biocompatible gas. Formation of fibrin foam is done by incorporating a biocompatible gas to the precursor solutions during the crosslinking of the fibrin network. This could be done by the use of propellants as described in U.S. reissue patent No. RE39,321, the content of which is incorporated by reference. Or the incorporation of a biocompatible gas can be done by mechanically mixing the gas with the precursor solutions. The biocompatible gas must be physiologically acceptable, suitable for pharmacological applications, and may include conventionally recognized gas, for example, $CO_2$, $N_2$, air or inert gas, such as freon, under pressure or not. Preferably, the biocompatible gas is air. In the alternative, the dry fibrin components may be supplemented with material(s) which produce gas, and hence foaming, upon contact with the hydrating agent. In one preferred embodiment the volume of the fibrinogen solution is about 40 to 60% of the volume of the biocompatible gas. Preferably volume of the fibrinogen solution is about 50% of the volume of the biocompatible gas.

1. Fibrinogen

The first precursor solution contains fibrinogen, preferably in a concentration range between 10 to 130 mg fibrinogen per milliliter of precursor solution, more preferably between 30 to 120 mg fibrinogen per milliliter of precursor solution, even more preferably from between 40 to 110 mg fibrinogen per milliliter of precursor solution, and most preferably 50 mg fibrinogen per milliliter of precursor solution. Fibrinogen is preferably solubilised in an aqueous buffer solution. Even more preferably, The fibrinogen dilution buffer comprises water, sodium citrate, preferably at a concentration of 25 mM, niacinamid, preferably at a concentration of 50 mM and histidin, preferably at a concentration of 100 mM, and has a preferably a pH of 7.3.

2. Thrombin

The concentrations of the fibrinogen solution and/or the thrombin solutions have a significant effect on the density of the formed network and on the clotting or crosslinking speed of the final fibrin matrix or foam. Typically, the reduction of the amount of thrombin slows down the crosslinking process and contributes to form fibrin matrices or foams with a less dense network. Surprisingly, controlling the ratio of the amounts of thrombin and fibrinogen, leads to a more prolonged release of the growth factor, particularly where a high concentration of growth factor is incorporated in the matrix or the foam. Furthermore, the ratio of the amount of thrombin to fibrinogen provides fibrin matrices or foams with a less dense network which is more suitable for cellular infiltration or in-growth and thus for wound healing.

In a preferred embodiment, the second precursor solution contains thrombin, wherein the thrombin amount is less than 0.3 U.I. thrombin per mg of fibrinogen, preferably in a range between 0.04 to 0.28 I.U. thrombin per mg of fibrinogen, more preferably between 0.06 to 0.1 I.U. thrombin per mg of fibrinogen, and most preferably 0.08 I.U. thrombin per mg of fibrinogen. Thrombin is preferably solubilised in an aqueous buffer solution. Even more preferably, the thrombin dilution buffer comprises water, calcium chloride, preferably at a concentration of 40 mM, and sodium chloride, preferably at a concentration of 75 mM, and has preferably a pH of 7.3.

3. Calcium Source

A calcium ion source may be present in at least one of the precursor solutions and preferably in the second precursor solution. The calcium ion source is preferably $CaCl_2 * 2H_2O$, preferably in a concentration range between 1 to 10 mg per ml of precursor solution, even more preferable between 4 to 7 mg per ml of precursor solution, most preferably between 5 to 6 mg per ml of precursor solution.

4. Crosslinking Enzymes

An enzyme capable of catalyzing the matrix formation after it has been activated, such as factor XIII, may be added to at least one of the precursor solution. Preferably, factor XIII is present in the fibrinogen precursor solution in a concentration range between 0.5 to 100 I.U. per millilitre of precursor solution, more preferably between 1 to 60 I.U. per millilitre of precursor solution, and most preferably between 1 to 10 I.U. per millilitre of precursor solution.

B. Fusion Proteins

In order to sequester growth factors, it is necessary to modify the protein so that it becomes capable of attaching to fibrin. This can be accomplished in several ways. By way of example, this may be achieved through the addition of a factor XIII substrate to the resulting fusion protein. Optionally, the fusion protein may contain a degradation site.

Preferred growth factors are members of the transforming growth factor (TGF β) superfamily and members of the platelet derived growth factor (PDGF) superfamily. In particular, preferred members are PDGF, PDGF A, PDGF B, PFGF D, PDGF BB, PDGF AB, TGFβ, BMP, VEGF, and Insulin-like growth factor (IGF) and most preferred are PDGF AB, TGFβ1, TGFβ3, BMP2, BMP7, VEGF 121 and IGF 1.

In a preferred embodiment, the fusion protein comprises an amino acid sequence of SEQ ID NO:2 and SEQ ID NO:3 (referred herein as TG-PDGF).

Additional amino acid sequences may be added to the growth factor to include a degradation site and/or a substrate for a crosslinking enzyme (referred to hereinafter as the "TG-degr"-hook). The amino acid sequence is selected based on the structure of the growth factor. In case the growth factors are hetero- or homodimeric, the additional amino acids can be attached to the termini of either one or both of the chains. In the preferred embodiment, the TG-degr-sequence is attached to both chains. Depending on the structure of the growth factor, i.e., the location of the active centers within the protein, the TG-degr-sequence can be attached to the N and/or C-terminus of the chains. In a preferred embodiment, the TG-degr-sequence is attached to the N-terminus. When the growth factor is PDGF AB (heterodimeric) or TGFβ1 (homodimeric), the TG-degr-sequence is attached to the N-terminus of both chains.

The addition of a synthetic factor XIIIa substrate can be accomplished by expressing a fusion protein containing the native growth factor sequence and a factor XIIIa substrate at either the amino or carboxyl terminus of the fusion protein. This modification is done at the DNA level. Whole proteins present difficulty in that they are synthesized by solid phase chemical synthesis. The DNA sequence encoding the growth factor is adapted to optimal codon usage for bacterial expression. The DNA sequence is then determined for the desired Factor XIIIa substrate, using codons which occur frequently in bacterial DNA.

A series of gene fragments is designed prior to the DNA synthesis. Due to the error frequency of most DNA synthesis, which contains an error approximately every 50 bp, genes are constructed to be approximately 100 bp in length. This reduces the number of colonies that must be screened in order to find one containing the proper DNA sequence. The location at which one gene ends and the next begins is selected based on the natural occurrence of unique restriction enzyme cut sites within the gene, resulting in fragments (or oligonucleotides) of variable length. The process is greatly assisted by the use of software which identifies the location and frequency of restriction enzyme sites within a given DNA sequence.

Once the gene fragments have been successfully designed, common restriction enzyme sites are included on the ends of each fragment to allow ligation of each fragment into a cloning plasmid. For example, adding EcoRI and HindIII sites to each gene fragment allows it to be inserted into the polylinker cloning region of pUC 19. The 3' and 5' single strands of each gene fragment are then synthesized using standard solid phase synthesis with the proper sticky ends for insertion into the cloning vector. Following cleavage and desalting, the single stranded fragments are then purified by PAGE and annealed. After phosphorylation, the annealed fragments are ligated into a cloning vector, such as pUC 19.

Alternatively, two DNA molecules can be spliced together using overlap extension PCR (Mergulhao et al. Mol Biotechnol. 1999 October; 12(3):285-7). First, genes are amplified by means of polymerase chain reactions (PCR) carried out on each molecule using oligonucleotide primers designed so that the ends of the resultant PCR products contain complementary sequences. When the two PCR products are mixed, denatured and reannealed, the single-stranded DNA strands having the complementary sequences anneal and then act as primers for each other. Extension of the annealed area by DNA polymerase produces a double-stranded DNA molecule in which the original molecules are spliced together. Gene splicing by overlap extension (SOE), provides for recombining DNA molecules at precise junctions irrespective of nucleotide sequences at the recombination site and without the use of restriction endonucleases or ligase. The SOE approach is a fast, simple, and extremely powerful, way of recombining and modifying nucleotide sequences.

Following ligation, the plasmids are transformed into DH5-F' competent cells and plated on Isopropyl-D-Thiogalactopyranoside(IPTG)/Bromo-4-chloro-3-indolyl-D-Galactopyranoside (X-gal) plates to screen for insertion of the gene fragments. The resulting colonies which contain gene fragment are then screened for insertion of the proper length. This is accomplished by purifying plasmid from colonies of transformed cells by alkaline lysis miniprep protocol and digesting the plasmid with the restriction enzyme sites present at either end of the gene fragment. Upon detection of the fragments of the proper length by agarose gel electrophoresis, the plasmids are sequenced.

When a plasmid containing a gene fragment with the proper sequence is identified, the fragment is then cut out and used to assemble the full gene. Each time one plasmid is cut with the enzymes at the insertion points and purified from an agarose gel after dephosphorylation of the plasmid. Meanwhile, a second plasmid containing the fragment to be inserted is also cut and the fragment to be inserted is purified from an agarose gel. The insert DNA is then ligated into the dephosphorylated plasmid. This process is continued until the full gene is assembled. The gene is then moved into an expression vector, such as pET 14b and transformed into bacteria for expression. After this final ligation, the full gene is sequenced to confirm that it is correct.

Expression of the fusion protein is accomplished by growing the bacteria until they reach mid-log phase growth and then inducing expression of the fusion protein. Expression is continued for approximately 3 hours and the cells are then harvested. After obtaining a bacterial cell pellet, the cells are lysed. The cell membranes and debris are removed by washing the cell lysate pellet with TRITON® X 100 (Polyethylene glycol octylphenyl ether, Poly(ethylene oxide)), leaving the inclusion bodies in relatively pure form. The fusion protein is solubilized using high urea concentrations and purified by histidine affinity chromatography. The resulting protein is then renatured gradually by dialysis against a slowly decreasing amount of urea and lyophilized.

III. Methods for Incorporation and/or Release of Fusion Proteins

The disclosed fusion protein supplemented fibrin matrices or foams are formed by coagulation of fibrinogen. A calcium source, thrombin, fibrinogen and at least one fusion protein form the supplemented fibrin matrix. In another embodiment, a calcium source, thrombin, fibrinogen, at least one fusion protein and a biocompatible gas form the supplemented fibrin foam Exogenous peptides can be designed as fusion proteins which include two domains, where the first domain is a bioactive factor, such as a peptide, protein, or polysaccharide, and the second domain is a substrate for a crosslinking enzyme, such as Factor XIIIa. Factor XIIIa is a transglutaminase that is active during coagulation. This enzyme, formed naturally from factor XIII by cleavage by thrombin, functions to attach fibrin chains to each other via amide linkages, formed between glutamine side chains and lysine side chains. Factor XIIIa also attaches other proteins to fibrin during coagulation, such as the protein alpha 2 plasmin inhibitor. The N-terminal domain of this protein, specifically the sequence NQEQVSP (SEQ ID NO:1), has been demonstrated to function as an effective substrate for factor XIIIa. A second domain of this peptide can contain a bioactive factor, such as a peptide, protein, or a polysaccharide (see Sakiyama-Elbert, et al., (2000) J. Controlled Release 65:389-402). Such fusion proteins may be used to incorporate bioactive factors (e.g. growth factors) within fibrin during coagulation via a factor XIIIa substrate.

Surprisingly, reducing the amount of thrombin (keeping the amount of fibrinogen constant) allows for prolonged controlled release of the fusion protein from the fibrin matrix or foam. Reducing the amount of thrombin allows for a control on the amount of growth released over time and a control of the rate of release of the growth factor. This effect is independent to the amount of growth factor initially incorporated in the fibrin matrix or foam. In one preferred embodiment, thrombin is used in an amount of less than 0.3 I.U. thrombin per mg of fibrinogen, preferably in a range between 0.04 to 0.28 I.U. thrombin per mg of fibrinogen, more preferably between 0.06 to 0.1 I.U. thrombin per mg of fibrinogen, and most preferably 0.08 I.U. thrombin per mg of fibrinogen. The fusion protein includes a first domain having a growth factor and a second domain having a transglutaminase substrate domain. In a preferred embodiment the Transglutaminase substrate domain is a factor XIIIa substrate domain. In a general method for preparing a fibrin matrix comprising at least one fusion protein covalently linked onto it, the method includes the steps of:

(i) providing a fibrinogen solution;
(ii) providing a thrombin solution wherein the amount of thrombin is less than 0.3 I.U. thrombin per mg of fibrinogen;
(iii) providing at least one fusion protein comprising a first domain comprising a bioactive factor and a second domain comprising a transglutaminase substrate domain; and
(iv) mixing components provided in steps (i), (ii) and (iii) to crosslink the matrix material such that the fusion protein is covalently linked to the matrix through the second domain.

The matrix can be in a form selected from the group consisting of a gel, a hydrogel, a film, a paste, a cream, a spray, an ointment, a wrap or a bandage or in certain embodiments the matrix can be in a form of a foam.

In a general method for preparing a fibrin foam comprising at least one fusion protein covalently linked onto it, the method includes the steps of:

(i) providing a fibrinogen solution;
(ii) providing a thrombin solution wherein the amount of thrombin is less than 0.3 I.U. thrombin per mg of fibrinogen;
(iii) providing at least one fusion protein comprising a first domain comprising a platelet derived growth factor (PDGF) and a second domain comprising a transglutaminase substrate domain;
(iv) providing a biocompatible gas; and
(v) mixing components provided in steps (i), (ii), (iii) and (iv) to form a fibrin matrix.

The controlled delivery fibrin matrix or foam obtained are characterized in that no more than 25% of growth factor is released after incubation of the controlled delivery fibrin foam during 3 days at 37° C. in a buffer solution.

In one embodiment, the fusion protein amount is in range from about 1 to 20 µg/mg of fibrinogen, preferably from about 1.32 to 16 µg/mg of fibrinogen, even more preferably from about 4 to 12 µg/mg of fibrinogen.

In a preferred embodiment, the fibrin matrix or foam are crosslinked in situ in or on the body. The fibrinogen and thrombin precursor solutions should be separated prior to application of the mixture to the body to prevent combination or contact with each other under conditions that allow polymerization of the solutions. To prevent contact prior to administration, a kit which separates the solutions from each other may be used. Upon mixing under conditions that allow polymerization, the compositions form a fusion protein supplemented fibrin matrix or foam. Depending on the precursor solutions and their concentrations, crosslinking can occur quasi-instantaneously after mixing. Such a fast crosslinking, makes the application or injection, i.e. squeezing of the gelled or foamed material through the injection needle, almost impossible.

Surprisingly, amounts of thrombin and fibrinogen such that the amount of thrombin is less than 0.3 I.U. thrombin per mg of fibrinogen are suitable for forming a fibrin foam supplemented with covalently linked growth factors. Upon mixing of the precursor solutions crosslinking occurs fast enough to produce a foam that solid enough to run off from the surface where it is applied and slow enough for allowing the foam to be applied or injected at the site of need before full crosslinking and clogging of the application or injection device. This method and the ratio of thrombin and fibrinogen are well suited to apply or inject the material in less than 1 minute from the mixing of the precursor solutions, preferably in less than 30 seconds and more preferably within 15 seconds. The applied or injected fibrin foam is adhesive enough to stay at the administration site and is malleable enough to be administered with the desired shape. In one embodiment the matrix is formed from fibrinogen. Fibrinogen, through a cascade of various reactions gels to form a matrix, when brought in contact with thrombin and a calcium source at appropriate temperature and pH. The three components, fibrinogen, thrombin, and the calcium source, should be stored separately. However, as long as at least one of the three components is kept separated the other two components can be combined prior to administration.

In one embodiment, fibrinogen, which may also contain aprotinin to increase stability, is dissolved in a buffer solution at physiological pH, ranging from pH 6.5 to 8.0, preferably ranging from pH 7.0 to 7.5. The buffer solution for the fibrinogen can comprises water, sodium citrate, preferably at a concentration of 25 mM, niacinamid, preferably at a concentration of 50 mM and histidine, preferably at a concentration of 100 mM, and has a preferably a pH of 7.3. Thrombin in a calcium chloride buffer (e.g. concentration range of from 40 to 50 mM) is prepared. The fibrinogen is then stored separately from the thrombin solution. The fibrinogen and the thrombin solutions can be stored frozen to enhance storage stability. Prior to use the fibrinogen solution and the thrombin solution are defrosted (when necessary) and mixed. In another embodiment, fibrinogen and thrombin can be stored separately from the calcium source. In still another embodiment, the fibrinogen can be stored with the calcium source and separated from the thrombin.

IV. Kits

In another embodiment, a kit, which contains a fusion protein, fibrinogen, thrombin, a calcium source and optionally a biocompatible gas, is provided. Optionally, the kit may contain a crosslinking enzyme, such as Factor XIIIa. The fusion protein contains a growth factor, a substrate domain for a crosslinking enzyme and optionally a degradation site between the substrate domain and bioactive factor. The fusion protein may be present in either the fibrinogen or the thrombin solution. In a preferred embodiment the fibrinogen solution contains the fusion protein. The biocompatible gas may be present in either the fibrinogen solution or the thrombin solution. Preferably, the biocompatible gas is present in the thrombin solution. The solutions and optionally the biocompatible gas are preferably mixed by a two way syringe device, in which mixing occurs by squeezing the contents of both syringes through a mixing chamber and/or needle and/or static mixer.

In a preferred embodiment both fibrinogen and thrombin are stored separately in lyophilised form. Either of the two can contain the fusion protein. Prior to use, the fibrinogen dilution buffer is added to the lyophilized fibrinogen, the buffer may additionally contain aprotinin. The lyophilized thrombin is dissolved in the calcium chloride solution. Subsequently, the fibrinogen and the thrombin solutions are placed in separate containers/vials/syringe bodies and mixed by a two way connecting device, such as a two-way syringe. Optionally, the containers/vials/syringe bodies are bipartite thus having two chambers separated by an adjustable partition which is perpendicular to the syringe body wall. One of the chambers contains the lyophilised fibrinogen or thrombin, while the other chamber contains an appropriate buffer solution. When the plunger is pressed down, the partition moves and releases the buffer into the fibrinogen chamber to dissolve the fibrinogen. In order to form a fibrin foam, a biocompatible gas can be added to any of the containers/vials/syringe bodies containing the fibrinogen solutions or the thrombin solutions. Once both fibrinogen and thrombin are dissolved, both bipartite syringe bodies are attached to a two way connecting device and the contents are mixed by squeezing them through the injection needle attached to the connecting device. Optionally, the connecting device contains a static mixer to improve mixing of the contents.

In a preferred embodiment the volume of the fibrinogen solution is about 40 to 60% of the volume of the biocompatible gas, preferably 50% prior to mixing. This ratio results in window of approximately 15 seconds during which the foaming process has started and produces a surface adhesive material that can be applied or injected at the site of need before full crosslinking has occurred. This allows applying the material to a surface which is not horizontal and preventing the material to run off the surface. This is particularly useful for wound healing indication where the surface to be treated is not horizontal such as the feet or legs of a patient.

In another preferred embodiment the fibrinogen is used in an amount of 50 mg/ml, thrombin is used in an amount of 4 I.U./ml and TG-PDGF.AB is used in an mount ranging from 1 to 600 µg/ml prior to mixing. This ratio results in an amount of up to 25% fusion protein released after incubation of the controlled delivery fibrin matrix or foam during 3 days at 37° C. in a buffer solution.

V. Methods of Use

The disclosed fusion protein supplemented fibrin matrices or foams can be used for repair, regeneration, or remodeling of tissues, and/or release of bioactive factors, prior to or at the time of implantation.

The controlled delivery matrices or foams of the present invention can be used in the treatment of a wound, preferably wherein the wound is an ulcer caused by diabetes.

Cells can also be added to the matrix prior to or at the time of implantation, or even subsequent to implantation, either at or subsequent to crosslinking of the polymer to form the matrix. This may be in addition to or in place of crosslinking the matrix to produce interstitial spacing designed to promote cell proliferation or in-growth.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Formation of TG-PDGF.AB

PDGF AB used in these experiments consisted of a PDGF A chain of 110 amino acids and a PDGF B chain of 109 amino acids. This form of PDGF AB (without TO-hook) can be found naturally in the human body.

The PDGF AB sequence was modified to allow for covalent binding to a fibrin matrix. Additional 21 amino acids, the TG-hook containing a plasmin degradation site, were attached to both of the N termini of the PDGF AB, as follows:

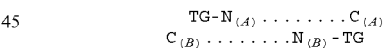

N refers to the N-terminus; C refers to the C-terminus; (A) refers to the A-chain; and (B) refers to the B-chain.

The amino acid sequence of TG-PDGF A is:

```
                                              (SEQ ID NO: 2)
MNQEQVSPLPVELPLIKMKPHSIEEAVPAVCKTRTVIYEIPRSQVDPTSA

NFLIWPPCVEVKRCTGCCNTSSVKCQPSRVHHRSVKVAKVEYVRKKPKLK

EVQVRLEEHLECACATTSLNPDYREEDTDVR.
```

The amino acid sequence of TG-PDGF B is:

```
                                              (SEQ ID NO: 3)
MNQEQVSPLPVELPLIKMKPHSLGSLTIAEPAMIAECKTRTEVFEISRRL

IDRTNANFLVWPPCVEVQRCSGCCNNRNVQCRPTQVQLRPVQVRKIEIVR

KKPIFKKATVTLEDHLACKCETVAAARPVT.
```

The A chain and the B chain of the heterodimer TG-PDGF AB were expressed separately in a bacterial system. The inclusion bodies of the bacteria cells were solubilized to release the A or the B chain, respectively. Both, the A and B chain solution were purified (separately) by using a cationic exchange column. Subsequently the A and the B chain were reduced/denaturized and precipitated. The precipitates were dissolved and the A and the B chain solution were mixed for the refolding step. The refolding to TG-PDGF.AB occurred in a buffer solution over a period of three to five days. The refolded protein was purified by a two step purification process, which contained a cationic exchange column followed by a gel filtration column.

Release Study Protocol

For each experiment, 100 µL-gels were made in triplicates using the DuPloject™ devices from Baxter. These 2-syringe devices allow mixing of equal amounts of the fibrinogen solution containing TG-PDGF.AB and the thrombin solution contained in the two syringes. One syringe contains the fibrinogen solution. The first precursor solution is prepared by diluting the fibrinogen component of the TISSEEL VHTM or VH S/DTM (S/D being an added virus inactivation step to provide added safety) from Baxter AG (Vienna, Austria) in buffer solution containing water, sodium citrate 25 mM, niacinamid 50 mM and histidin 100 mM to a concentration of 50 mg/ml of fibrinogen. The first precursor solution has a pH of 7.3. TG-PDGF.AB is added to the fibrinogen precursor solution at concentration of 66, 200 or 600 µg/ml. The second syringe contains thrombin obtained from TISSEEL VHTM or VH S/DTM (S/D being an added virus inactivation step to provide added safety) from Baxter AG (Vienna, Austria) (with different amounts as indicated in the examples) diluted in a buffer containing calcium chloride 40 mM) and sodium chloride 75 m to final thrombin concentrations of 4, 15, 31, 62, 125 and 250 IU/ml. The syringe solutions are mixed in equal volumes.

The gels were left drying at 37° C. for one hour. They were inserted in 15 ml-falcon tubes containing 10 ml release buffer (TRIS 10 mM, NaCl 70 mM, KCl 1.3 mM, BSA 0.1%, pH 7.4) and incubated for 72 hours in an incubator at 37° C. 100 µL release buffer aliquots were taken at appropriate time points (approximately 6, 24, 48 and 72 hours). PDGF-AB concentrations contained in the release buffer at different time points were determined using an in-house ELISA assay.

Example 1

Release Rates of High and Low Dose TG-PDGF.AB

A release study protocol was done 5 times (with the same or different lots, on different days) with fibrinogen solution containing either 66 or 600 µg/ml TG-PDGF.AB. An average release rate was calculated using these 5 experiments.

Figure 2:
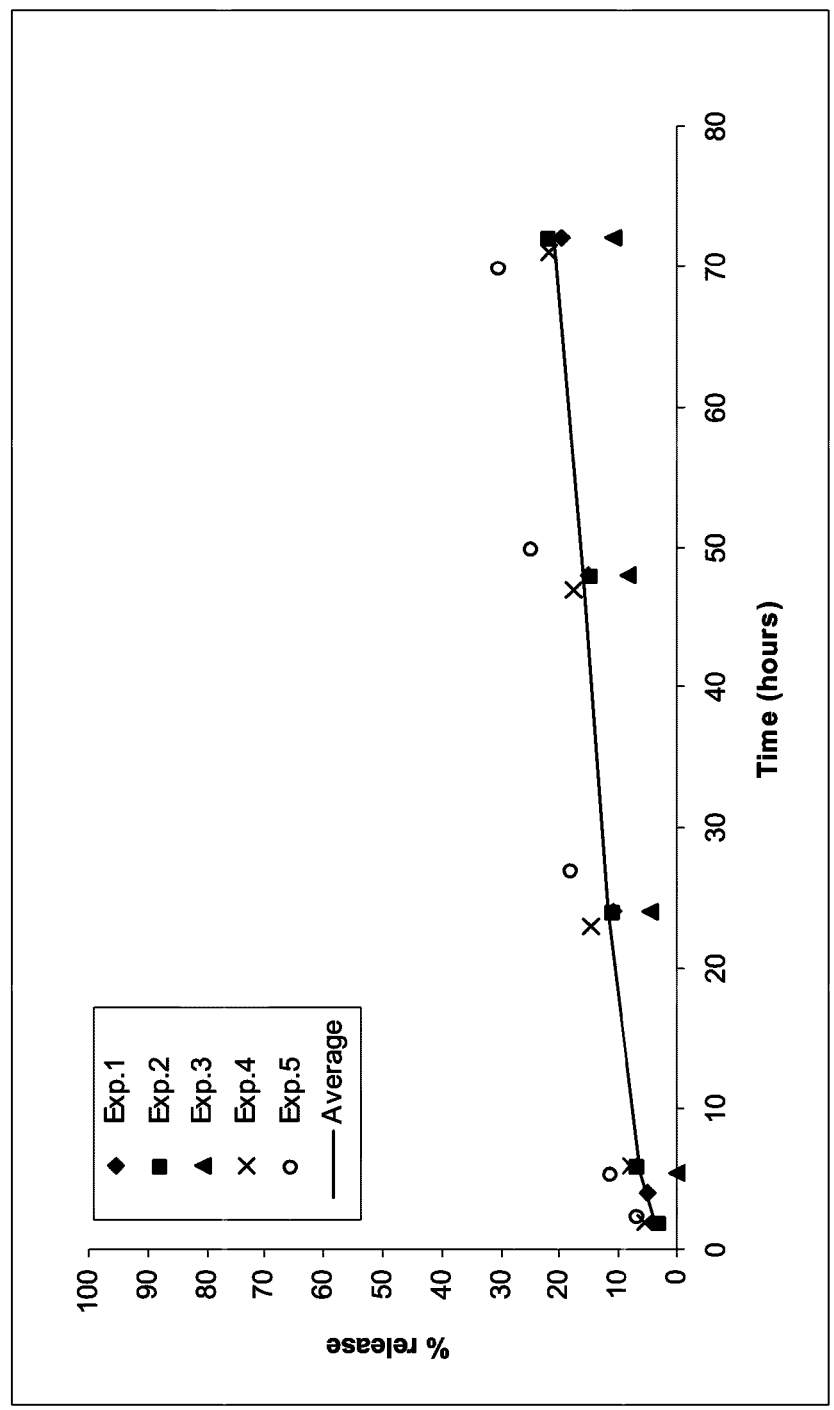
FIG. 2 is a line graph of the percent release of TG-PDGF.AB versus time (hours) from a fibrin matrix prepared with 50 mg/ml of fibrinogen, 250 I.U./ml of thrombin and 66 µg/ml of TG-PDGF.AB. Five experiments are plotted on the graph.

The release rate of the high dose (600 µg/ml TG-PDGF.AB in the fibrinogen solution) (FIG. 1) is much higher than the release rate of the low dose (66 µg/ml TG-PDGF.AB) (FIG. 2): 62% and 21% respectively.

Example 2

Influence of Thrombin Concentration on the Release of TG-PDGF.AB

Figure 3:
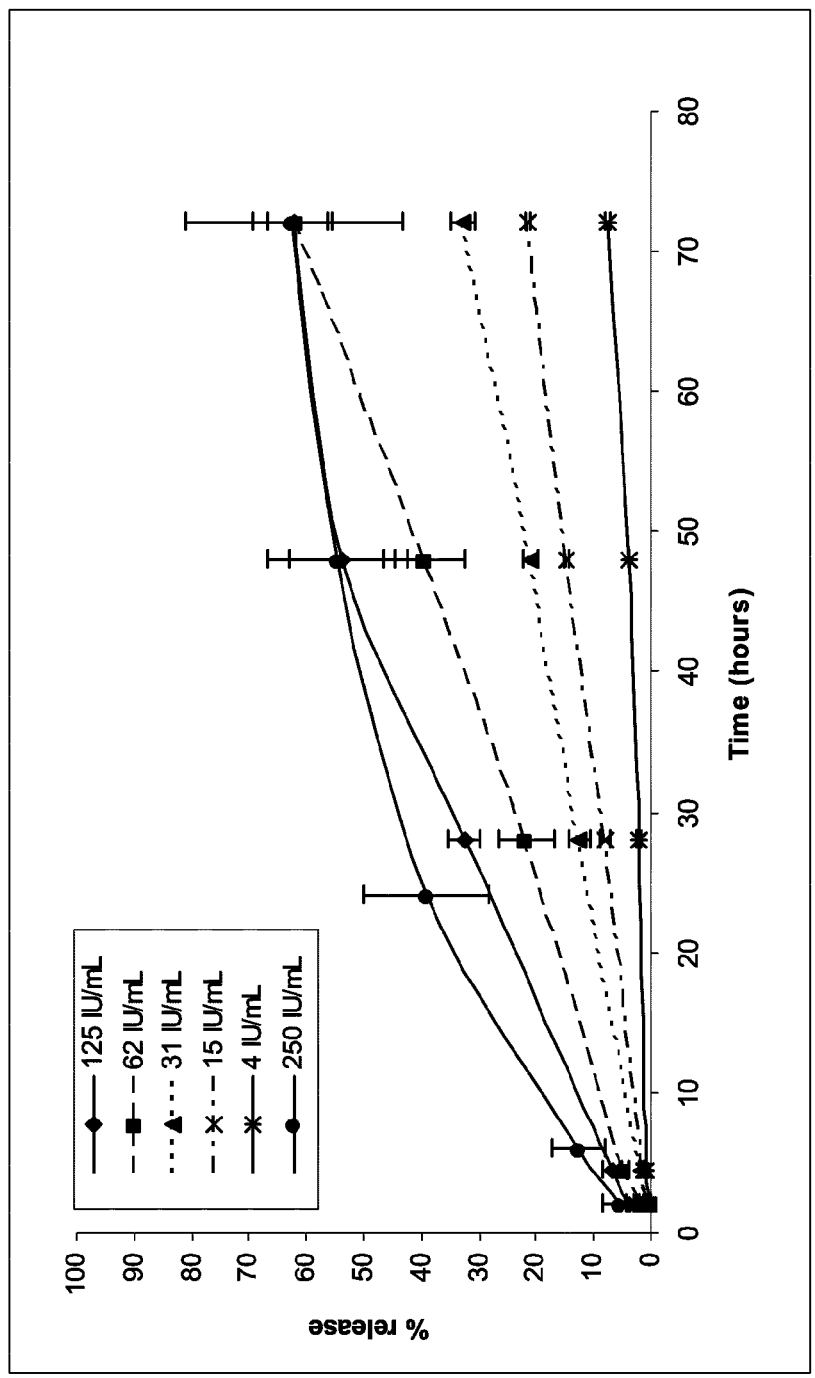
FIG. 3 is a line graph of the percent release of TG-PDGF.AB versus time (hours) from a fibrin matrix prepared with 50 mg/ml of fibrinogen, 600 µg/ml of TG-PDGF.AB and 4 I.U./ml (□), 15 I.U./ml (X)>31 I.U./ml (▲), 62 I.U./ml (■), 125 I.U./ml (♦) and 250 I.U./ml (●) of thrombin.
Figure 4:
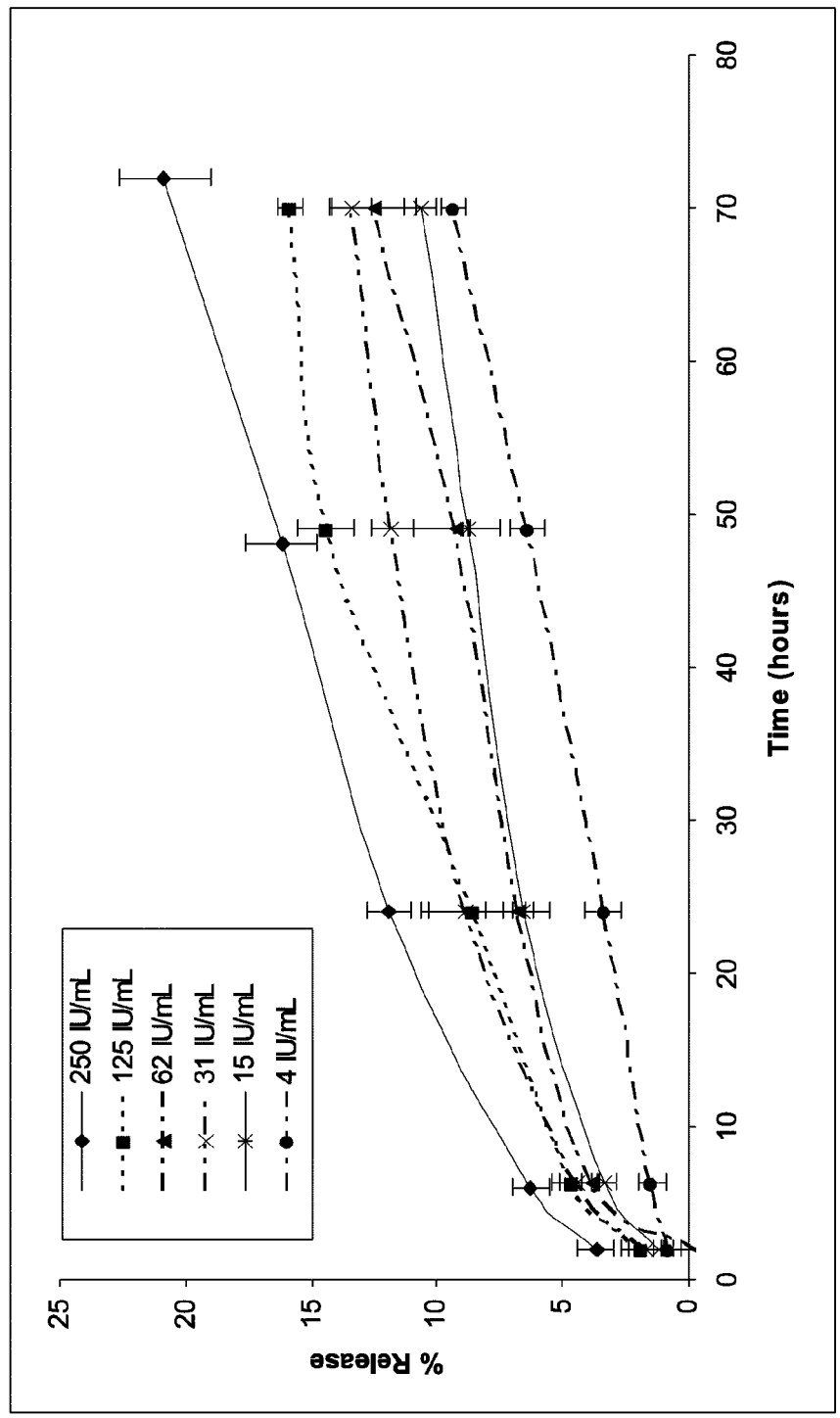
FIG. 4 is a line graph of the percent release of TG-PDGF.AB versus time (hours) from a fibrin matrix prepared with 50 mg/ml of fibrinogen, 66 µg/ml of TG-PDGF.AB and 4 I.U./ml (●), 15 I.U./ml (□), 31 I.U./ml (X), 62 I.U./ml (▲), 125 I.U./ml (■) and 250 I.U./ml (♦) of thrombin.

A release study was performed using different amounts of thrombin (4, 15, 31, 62, 125 and 250 IU/ml) in the thrombin solution, the fibrinogen solution remaining unchanged (50 mg/ml fibrinogen and 600 µg/ml TG-PDGF.AB for FIG. 3 and 66 µg/ml TG-PDGF.AB for FIG. 4).

Figure 5:
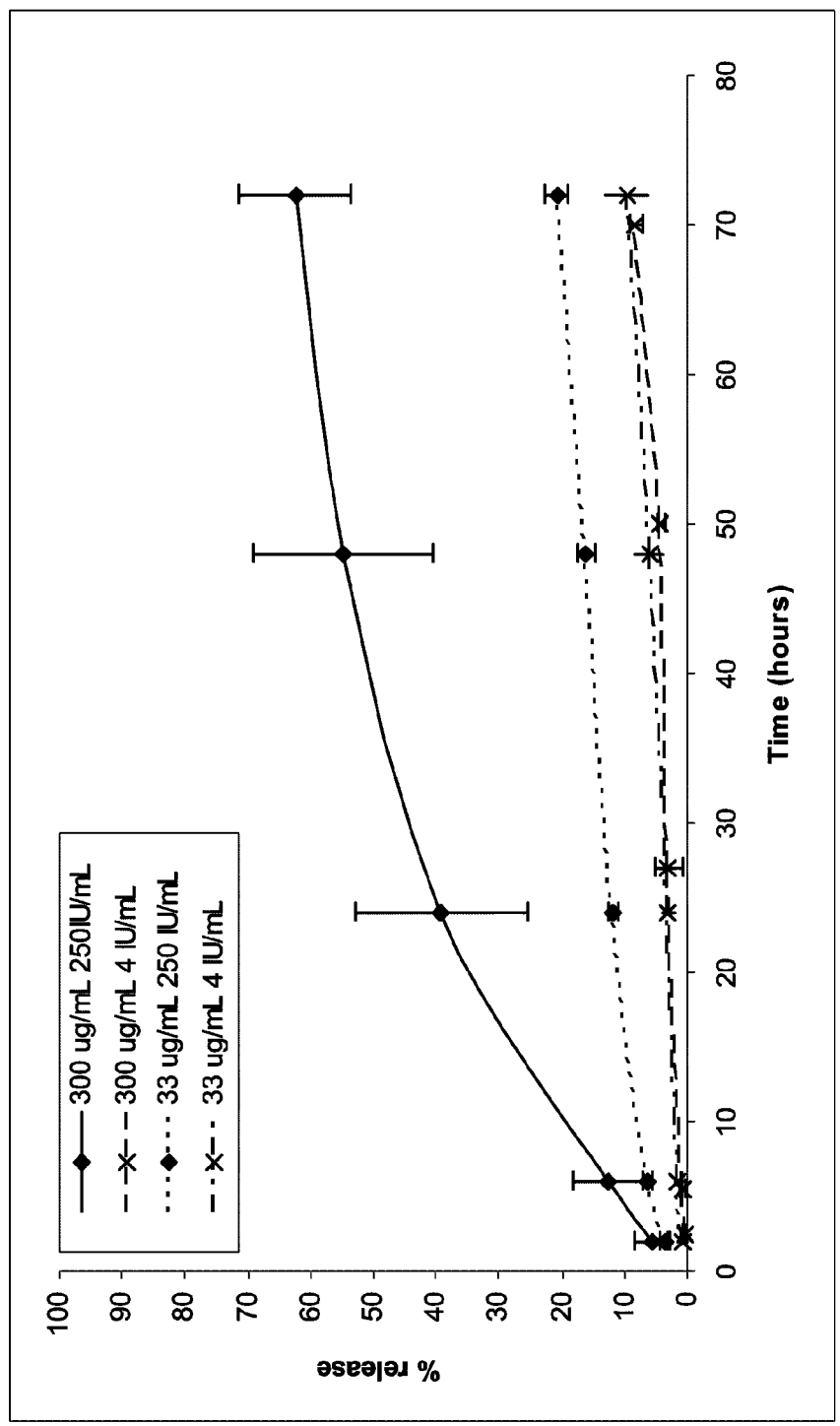
FIG. 5 is a line graph of the percent release of TG-PDGF.AB versus time (hours) from a fibrin matrix prepared with 50 mg/ml of fibrinogen, and 66 µg/ml (final concentration of 33 µg/ml) of TG-PDGF.AB and 4 I.U./ml and 250 I.U./ml of thrombin and a fibrin matrix prepared with 50 mg/ml of fibrinogen, 600 µg/ml of TG-PDGF.AB (final concentration 300 µg/ml) and 4 I.U./ml and 250 I.U./ml of thrombin.

Data corresponding to 250 IU/ml and 4 IU/ml thrombin of FIGS. 3 and 4 are presented are shown in FIG. 5. For both doses, decreasing the thrombin concentration leads to a lower release rate.

Example 3

Release Study with Differing Amounts of Factor XIII

A release study was performed adding different amounts of factor XIII in the fibrinogen solution (0, 0.2, 2 and 20 IU/ml ie 0, 0.1, 1 and 10 IU/ml in the final gel).

Figure 6:
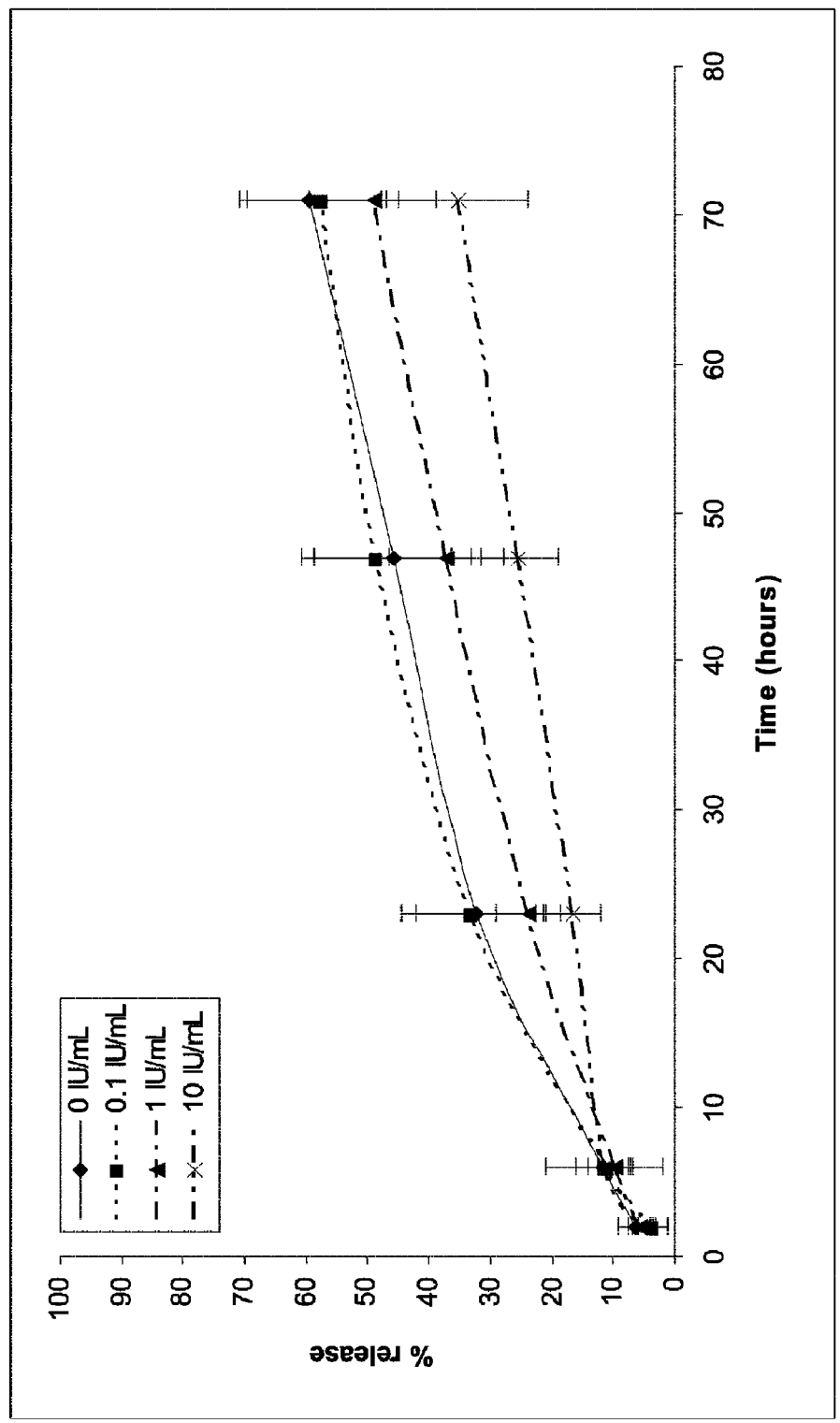
FIG. 6 is a line graph of the percent release of TG-PDGF.AB versus time (hours) from a fibrin matrix prepared with 50 mg/ml of fibrinogen, 600 µg/ml of TG-PDGF.AB and 250 I.U./ml of thrombin with factor XIII concentration of 0 I.U./ml (♦), 0.1 I.U./ml (■), 1 I.U./ml (▲) and 10 I.U./ml (X).
Figure 7:
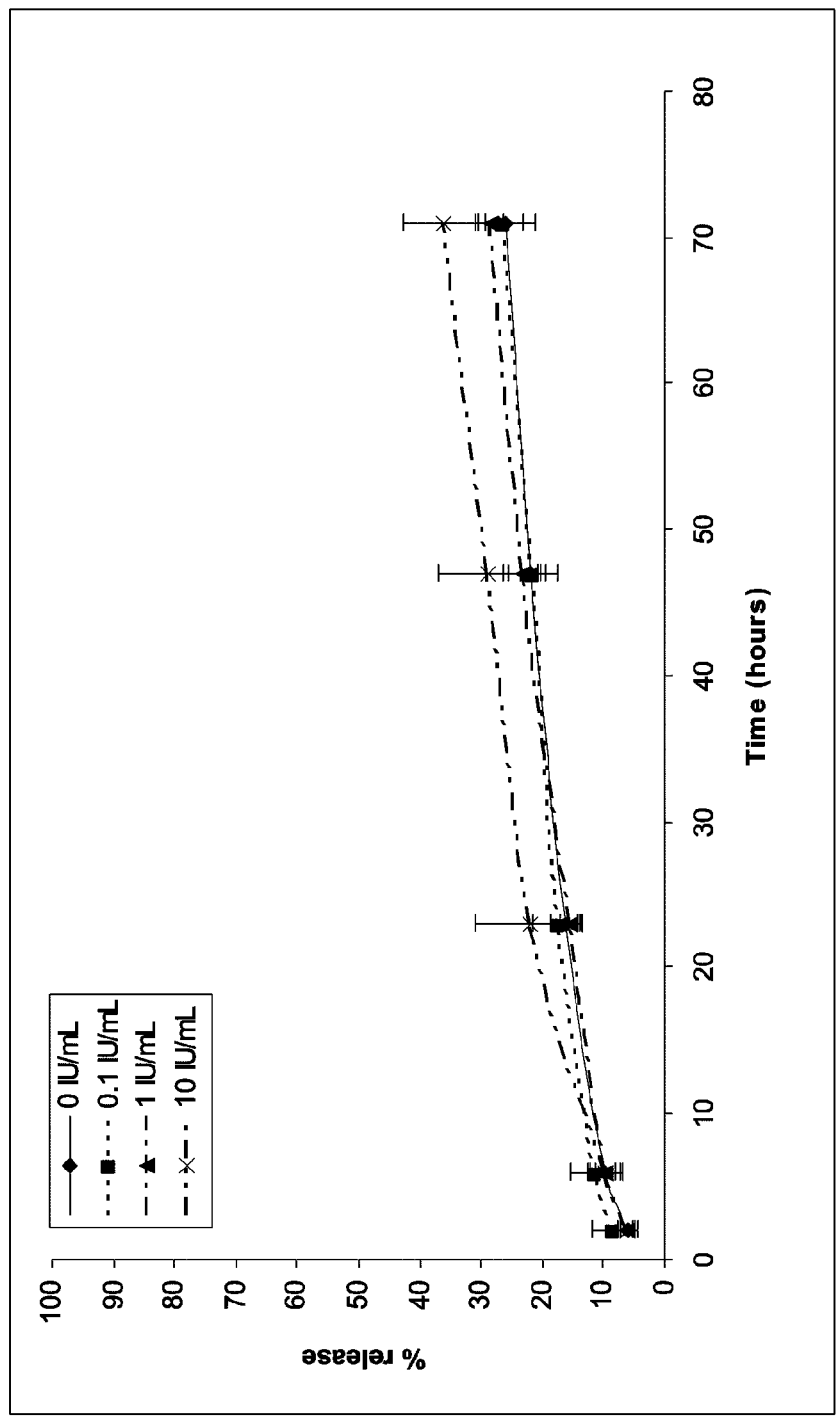
FIG. 7 is a line graph of the percent release of TG-PDGF.AB versus time (hours) from a fibrin matrix prepared with 50 mg/ml of fibrinogen, 66 µg/ml of TG-PDGF.AB and 250 I.U./ml of thrombin with factor XIII concentration of 0 I.U./ml (♦), 0.1 I.U./ml (■), 1 I.U./ml (▲) and 10 I.U./ml (X).
Figure 8:
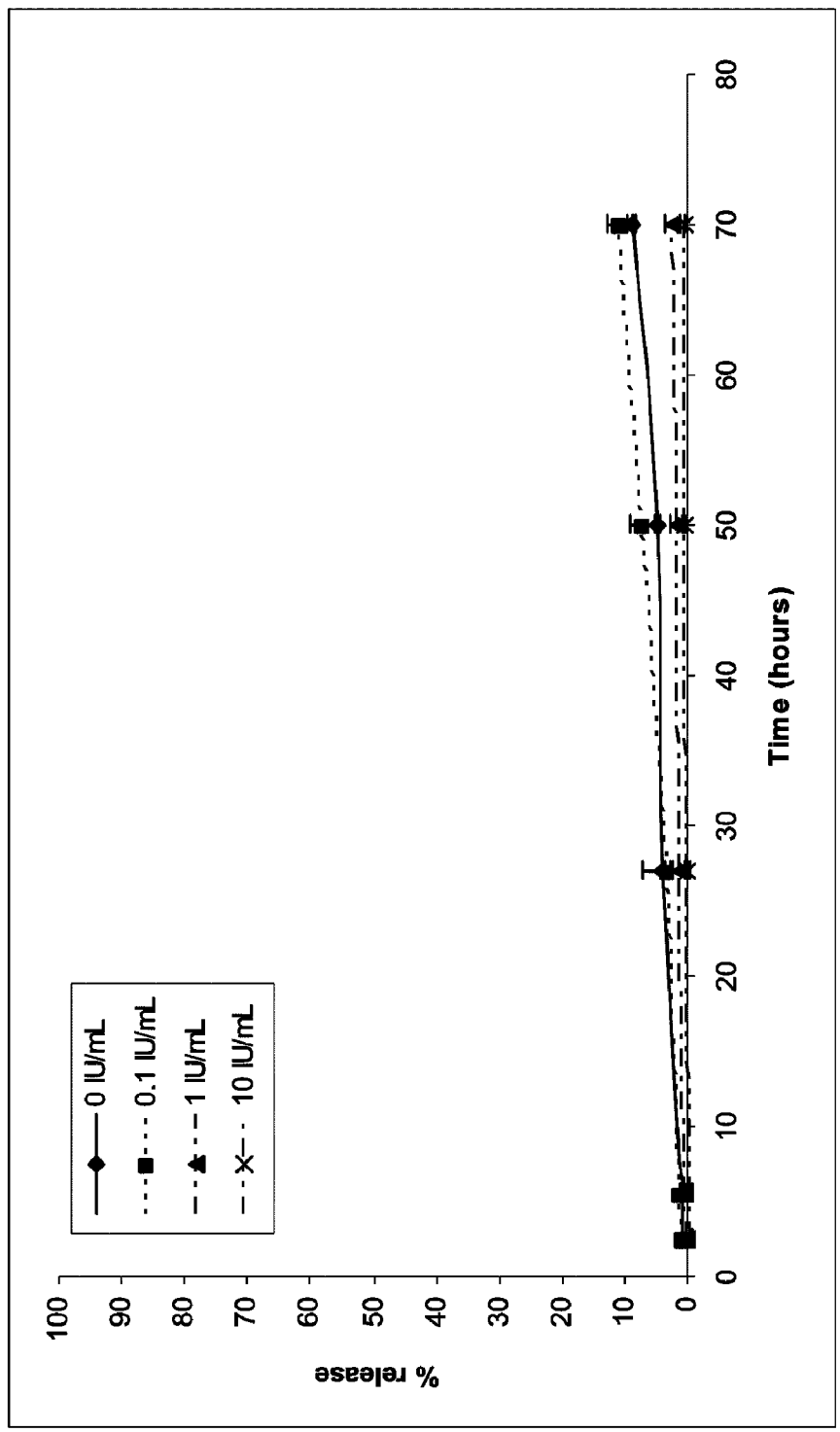
FIG. 8 is a line graph of the percent release of TG-PDGF.AB versus time (hours) from a fibrin matrix prepared with 50 mg/ml of fibrinogen, 600 µg/ml of TG-PDGF.AB and 4 I.U./ml of thrombin with factor XIII concentration of 0 I.U./ml (♦), 0.1 I.U./ml (■), 1 I.U./ml (▲) and 10 I.U./ml (X).
Figure 9:
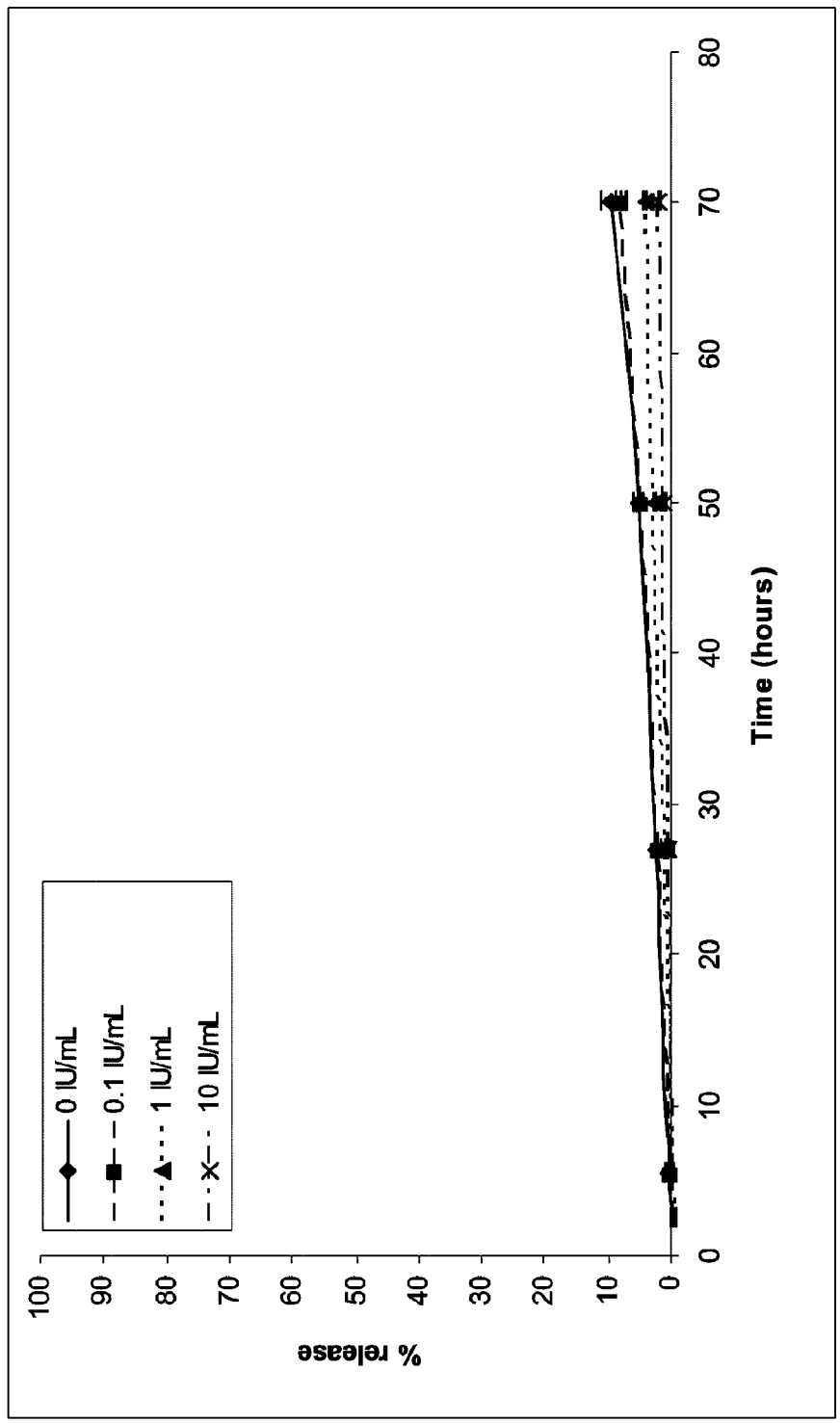
FIG. 9 is a line graph of the percent release of TG-PDGF.AB versus time (hours) from a fibrin matrix prepared with 50 mg/ml of fibrinogen, 66 µg/ml of TG-PDGF.AB and 4 I.U./ml of thrombin with factor XIII concentration of 0 I.U./ml (♦), 0.1 I.U./ml (■), 1 I.U./ml (▲) and 10 I.U./ml (X).

This experiment was done for the high (300 µg/ml TG-PDGF.AB in the fibrin gel) and low doses (33 µg/ml TG-PDGF.AB in the fibrin gel) with 250 IU/ml thrombin (FIGS. 6 and 7 respectively), and for the high and low doses with 4 IU/ml thrombin (FIGS. 8 and 9 respectively).

For 250 IU/ml thrombin, increasing factor XIII concentration leads to a lower release for the high dose of TG-PDGF.AB (60% to 35% release). This has no significant influence on the release rate for the low dose.

For 4 IU/ml thrombin, increasing factor XIII concentration has no influence on the release rate for both doses as the release rate is already low (around 10%).

Example 4

Release Study from Fibrin Foam

Material and Methods

The test items were prepared by mixing the content of two syringes through a mixer three times back and forth. The first syringe contained 0.5 ml of 50 mg/ml fibrinogen solution, the second contained 0.5 ml of 4 IU/ml thrombin solution and 1 ml of air.

6 (samples with buffer changed) or 4 replicates (sample with buffer not changed) of each test items were prepared. The test items were prepared in 2.5 ml syringes from which the ends had been cut, used as moulds. Samples were dried for 1 hour at 37° C. and weighed before being assayed in the buffer in order to estimate the total amount of TG-PDGF.AB contained in the initial test items.

Samples with buffer changed: the test items were incubated in 10 ml release buffer in 15 ml falcon tubes and 100 µL aliquots of this buffer were taken at each time point and frozen at −20° C. until further analysis. At each time-point (twice a day) and until complete degradation of the samples occurred, the buffer was removed and 10 ml fresh release buffer added to the samples.

Samples with buffer not changed: the test items were incubated in 10 ml release buffer in 15 ml falcon tubes and 500 µL aliquots of this buffer were taken at each time point and frozen at −20° C. until further analysis. The buffer was not changed at each time point.

An ELISA system was used to quantify TG-PDGF.AB and PDGF-AB contained in the buffer aliquots taken at the various time points. The PDGF-AB concentrations of the release samples were calculated from the Optical Density values obtained by ELISA, with all calculations performed and graphs plotted using Microsoft EXCEL.

Results

Figure 10:
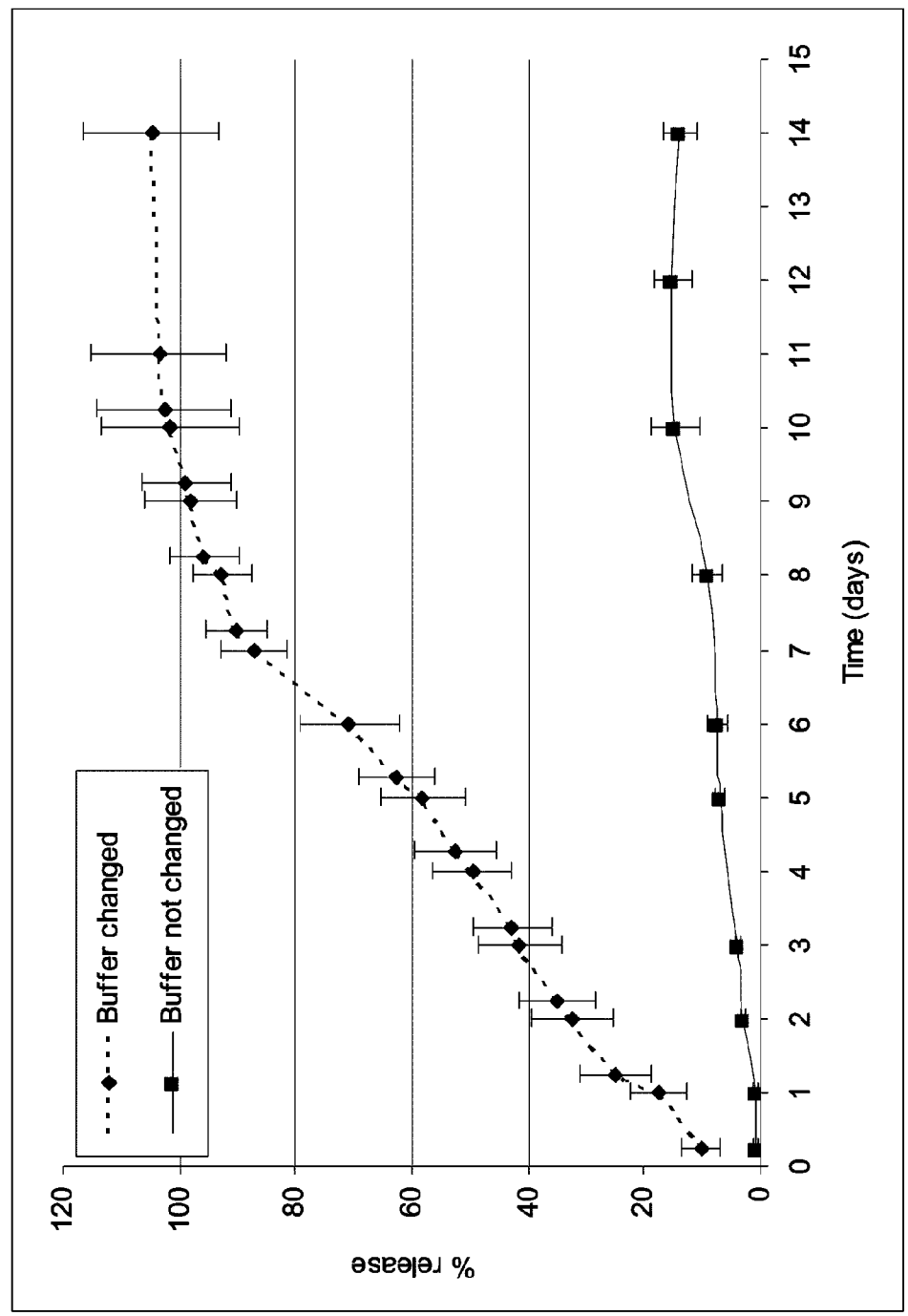
FIG. 10 is a release comparison of TG-PDGF.AB from test items incubated in buffer until full degradation (buffer changed (♦)) or over 14 days without degradation (buffer not changed (■)).

When the buffer was changed, the test items degraded (after 14 days, all samples had disappeared). On the opposite, if the buffer was not changed, the test items were intact (as assessed visually) after 14 days incubation in buffer. The percentage of TG-PDGF.AB or PDGF-AB released from each test items was calculated and plotted against time (see FIG. 10). The results show that 100% of TG-PDGF.AB initially incorporated in the test items were recovered upon degradation of the test items, whereas only 14% were released when buffer was not changed.

Example 5

Comparison of TG-PDGF.AB and Native PDGF-AB Release from Fibrin Foam

Fibrin foam clots were prepared as described in example 4 with 50% air of the total volume. The clots were weighed so as to determine the total amount of fibrin/TG-PDGF.AB contained in the fibrin foam clots (corresponding to 100% level on the graph). The fibrin foam clots were prepared in triplicates. Three TG-PDGF.AB concentrations were tested: 66, 200 and 600 µg/ml of fibrinogen. These concentrations correspond to 16.5, 50 and 150 µg/ml in the fibrin foam.

For understanding purposes, each of 66, 200 and 600 µg/ml TG-PDGF.AB concentrations is referred as low, middle and high dose of TG-PDGF.AB, respectively.

After preparation, the fibrin foam clots were incubated for 3 days at 37° C. in release buffer, and aliquots were taken at 4 time points: 6 h, 25 h, 48 h and 75 h. The concentration of PDGF contained in the release buffer at these time points was determined by ELISA.

Figure 11:
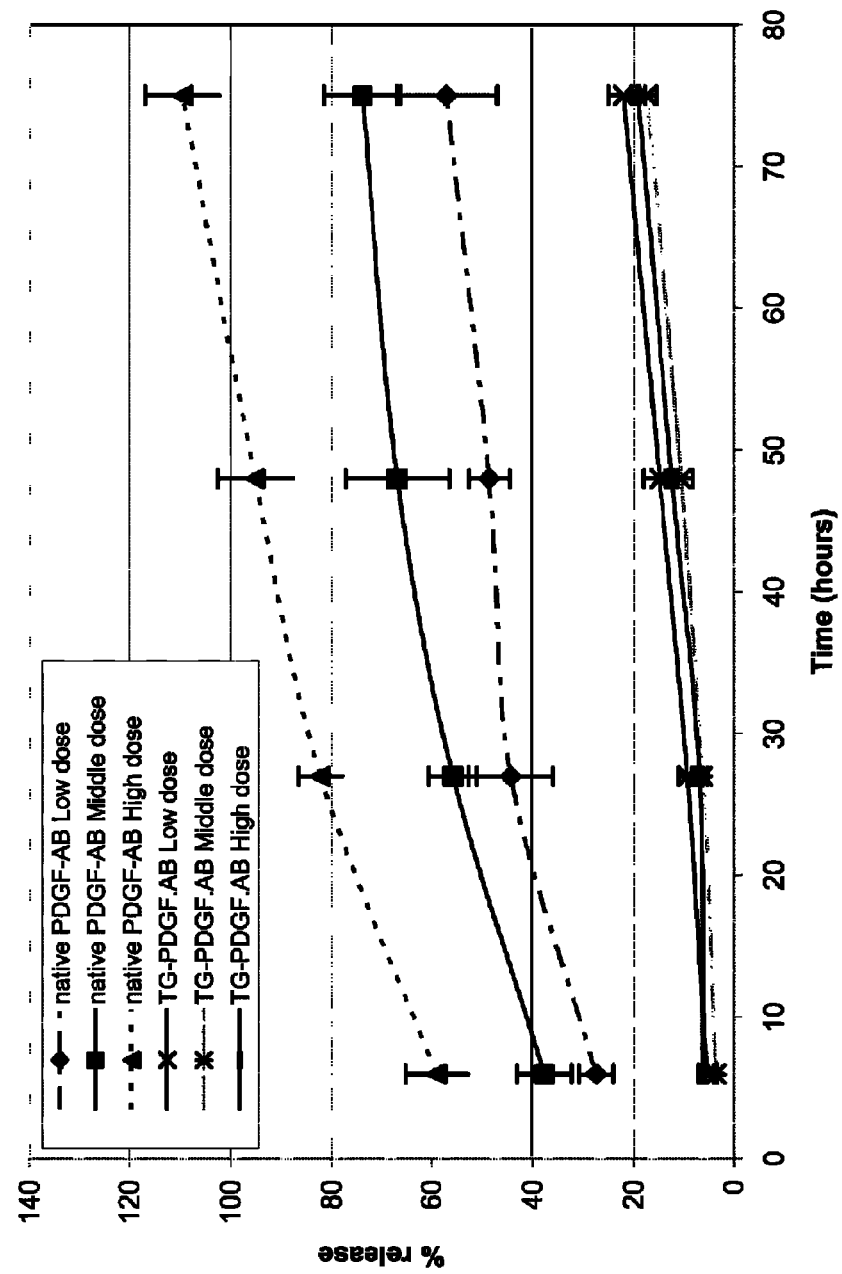
FIG. 11 is the release profile (% TG-PDGF.AB released vs time) of TG-PDGF.AB and native PDGF-AB from fibrin foam clots for three concentrations (High, Middle, Low doses). Native PDGF-AB low dose (♦), Native PDGF-AB middle dose (■), Native PDGF-AB high dose (▲) TG-PDGF.AB low dose (X), TG-PDGF.AB middle dose (□) and TG-PDGF.AB high dose (–).

FIG. 11 shows the release profiles of TG-PDGF.AB and native PDGF-AB from fibrin foam clots for all three concentrations.

First of all, TG-PDGF.AB was much less released from the fibrin foam clots than native PDGF.AB (release rates of TG-PDGF.AB versus native PDGF.AB was 22% vs 57%, 17% vs 74% and 19% vs 110% for low, middle and high doses).

Secondly, whereas there was no significant difference in the release rates of TG-PDGF.AB for all three doses, the release rates of native PDGF-AB from fibrin foam clots increased as the concentrations of native PDGF-AB increased.

We claim:

1. A foam composition comprising:
   fibrinogen;
   thrombin, wherein the amount of thrombin is less than 0.3 IU of thrombin/mg of fibrinogen;
   at least one fusion protein comprising a first domain comprising a platelet-derived growth factor (PDGF) and a second domain comprising a transglutaminase substrate domain;
   and a biocompatible gas selected from the group consisting of $CO_2$, $N_2$, air, and an inert gas, in an effective amount to form the foam.

2. The composition of claim 1, further comprising a calcium source.

3. The composition of claim 1, wherein the transglutaminase substrate domain comprises a Factor XIIIa substrate domain.

4. The composition of claim 3, wherein the Factor XIIIa substrate domain comprises SEQ ID NO:1.

5. The composition of claim 1, wherein the fusion protein further comprises a degradation site between the first and the second domain.

6. The composition of claim 5, wherein the degradation site is an enzymatic or hydrolytic degradation site.

7. The composition of claim 5, wherein the degradation site is an enzymatic degradation site which is cleaved by an enzyme selected from the group consisting of plasmin and matrix metalloproteinase.

8. The composition of claim 1, wherein the fusion protein comprises the amino acid sequence of SEQ ID NO:2 or SEQ ID NO:3.

9. The composition of claim 1, wherein the concentration of the fibrinogen solution is in a range of about 10 mg/ml to about 130 mg/ml.

10. The composition of claim 1, wherein the concentration of the fibrinogen solution is about 50 mg/ml.

11. The composition of claim 1, wherein the thrombin amount is from about 0.04 to about 0.28 IU thrombin per mg of fibrinogen.

12. The composition of claim 1, wherein the thrombin amount is about 0.08 IU thrombin per mg of fibrinogen.

13. The composition of claim 1, wherein the amount of the fusion protein is from about 4 to about 12 μg fusion protein per mg of fibrinogen.

14. A kit for forming a foam comprising:
   (i) a first container comprising fibrinogen and at least one fusion protein comprising a first domain comprising a platelet-derived growth factor (PDGF) and a second domain comprising a substrate domain for a crosslinking enzyme; and
   (ii) a second container comprising thrombin, wherein the amount of thrombin is less than 0.3 IU thrombin per mg of fibrinogen, and
   (iii) a biocompatible gas selected from the group consisting of $CO_2$, $N_2$, air, and an inert gas.

15. The kit of claim 14, further comprising a calcium source.

16. The kit of claim 14, wherein the biocompatible gas is either in the first or the second container.

17. The kit of claim 14, wherein the fusion protein comprises the amino acid sequence of SEQ ID NO:2 or SEQ ID NO:3.

18. The kit of claim 14, wherein the concentration of the fibrinogen solution is in a range of about 10 mg/ml to about 130 mg/ml.

19. The kit of claim 14, wherein the thrombin amount is from about 0.04 to about 0.28 IU thrombin per mg of fibrinogen.

20. The kit of claim 14, wherein the amount of the fusion protein is from about 4 to about 12 µg fusion protein per mg of fibrinogen.

21. A method for preparing a fibrin foam comprising at least one fusion protein, the method comprising the steps of:
   (i) providing a fibrinogen solution;
   (ii) providing a thrombin solution wherein the amount of thrombin is less than 0.3 IU thrombin per mg of fibrinogen;
   (iii) providing at least one fusion protein comprising a first domain comprising a platelet-derived growth factor (PDGF) and a second domain comprising a transglutaminase substrate domain;
   (iv) providing a biocompatible gas selected from the group consisting of $CO_2$, $N_2$, air, and an inert gas; and
   (v) mixing components provided in steps (i), (ii), (iii), and (iv) to form the fibrin foam thereby covalently linking the fusion protein to fibrin through the second domain.

22. The method of claim 21, further comprising the step of providing a calcium source.

23. The method of claim 21, wherein the biocompatible gas is air.

24. The method of claim 21, wherein the volume of the fibrinogen solution is about 40 to 60% of the volume of the biocompatible gas.

25. The method of claim 21, wherein the transglutaminase substrate domain comprises a Factor XIIIa substrate domain.

26. The method of claim 21, wherein the Factor XIIIa substrate domain comprises SEQ ID NO:1.

27. The method of claim 21, wherein the fusion protein further comprises a degradation site between the first and the second domain.

28. The method of claim 27, wherein the degradation site is an enzymatic or hydrolytic degradation site.

29. The method of claim 28, wherein the degradation site is an enzymatic degradation site, which is cleavable by an enzyme selected from the group consisting of plasmin and matrix metalloproteinase.

30. The method of claim 21, wherein the fusion protein comprises SEQ ID NO:2.

31. The method of claim 21, wherein the concentration of the fibrinogen solution is in a range of about 10 mg/ml to 130 mg/ml.

32. The method of claim 21, wherein the thrombin amount is from about 0.04 to 0.28 IU thrombin per mg of fibrinogen.

33. The method of claim 21, wherein the fusion protein amount is in the range of from about 4 to 12 µg/mg of fibrinogen.

34. A fibrin foam obtained by mixing
   (i) a fibrinogen solution;
   (ii) a thrombin solution, wherein the amount of thrombin is less than 0.3 I.U. thrombin per mg of fibrinogen;
   (iii) at least one fusion protein comprising a first domain comprising a platelet-derived growth factor (PDGF) and a second domain comprising a transglutaminase substrate domain; and
   (iv) a biocompatible gas selected from the group consisting of $CO_2$, $N_2$, air, and an inert gas, wherein the fusion protein is covalently linked to the fibrin.

35. The fibrin foam of claim 34 wherein no more than 25% of the PDGF is released after incubation of the fibrin foam during 3 days at 37° C. in a buffer solution.

36. A method for treating a wound comprising administering the fibrin foam of claim 34 to the wound.

37. The method of claim 36, wherein the wound is an ulcer caused by diabetes.

38. The kit of claim 14, wherein following mixing of the components in the kit, a fibrin foam is formed, wherein the foam releases no more than 25% of the PDGF after incubation during 3 days at 37° C. in a buffer solution.

39. The kit of claim 16, wherein the volume of the fibrinogen solution is about 40 to 60% of the volume of the biocompatible gas.

* * * * *

UNITED STATES PATENT AND TRADEMARK OFFICE
CERTIFICATE OF CORRECTION

PATENT NO.         : 8,226,942 B2                                    Page 1 of 1
APPLICATION NO.    : 12/342420
DATED              : July 24, 2012
INVENTOR(S)        : Gaëlle Charier, Manuela Müller-Maissen and Anna Jen It is certified that error appears in the above-identified patent and that said Letters Patent is hereby corrected as shown below:

Claim 35, column 22, line 24, delete the "." after "37° C".
Claim 38, column 22, line 32, delete the "." after "37° C".

Signed and Sealed this
Twenty-fifth Day of December, 2012

David J. Kappos
*Director of the United States Patent and Trademark Office*

```
                        SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic N terminal domain of alpha 2 plasmin
      inhibitor

<400> SEQUENCE: 1

Asn Gln Glu Gln Val Ser Pro
1               5

<210> SEQ ID NO 2
<211> LENGTH: 131
<212> TYPE: PRT
<213> ORGANISM: Artificial Sequence
<220> FEATURE:
<223> OTHER INFORMATION: Synthetic TG-PDGF A

<400> SEQUENCE: 2

Met Asn Gln Glu Gln Val Ser Pro Leu Pro Val Glu Leu Pro Leu Ile
1               5                   10                  15

Lys Met Lys Pro His Ser Ile Glu Glu Ala Val Pro Ala Val Cys Lys
            20                  25                  30

Thr Arg Thr Val Ile Tyr Glu Ile Pro Arg Ser Gln Val Asp Pro Thr
        35                  40                  45

Ser Ala Asn Phe Leu Ile Trp Pro Pro Cys Val Glu Val Lys Arg Cys
    50                  55                  60

Thr Gly Cys Cys Asn Thr Ser Ser Val Lys Cys Gln Pro Ser Arg Val
65                  70                  75                  80

His His Arg Ser Val Lys Val Ala Lys Val Glu Tyr Val Arg Lys Lys
                85                  90                  95

Pro Lys Leu Lys Glu Val Gln Val Arg Leu Glu Glu His Leu Glu Cys
            100                 105                 110

Ala Cys Ala Thr Thr Ser Leu Asn Pro Asp Tyr Arg Glu Glu Asp Thr
        115                 120                 125

Asp Val Arg
    130
```

```
<210> SEQ ID NO 3
<211> LENGTH: 130
<212> TYPE: PRT
<213> ORGANISM: Artificial Sequence
<220> FEATURE:
<223> OTHER INFORMATION: Synthetic TG-PDGF B

<400> SEQUENCE: 3

Met Asn Gln Glu Gln Val Ser Pro Leu Pro Val Glu Leu Pro Leu Ile
1               5                   10                  15

Lys Met Lys Pro His Ser Leu Gly Ser Leu Thr Ile Ala Glu Pro Ala
            20                  25                  30

Met Ile Ala Glu Cys Lys Thr Arg Thr Glu Val Phe Glu Ile Ser Arg
        35                  40                  45

Arg Leu Ile Asp Arg Thr Asn Ala Asn Phe Leu Val Trp Pro Pro Cys
    50                  55                  60

Val Glu Val Gln Arg Cys Ser Gly Cys Cys Asn Asn Arg Asn Val Gln
65                  70                  75                  80

Cys Arg Pro Thr Gln Val Gln Leu Arg Pro Val Gln Val Arg Lys Ile
                85                  90                  95

Glu Ile Val Arg Lys Lys Pro Ile Phe Lys Lys Ala Thr Val Thr Leu
            100                 105                 110

Glu Asp His Leu Ala Cys Lys Cys Glu Thr Val Ala Ala Ala Arg Pro
        115                 120                 125

Val Thr
    130
```